(12) United States Patent
Harris et al.

(10) Patent No.: US 11,590,008 B2
(45) Date of Patent: *Feb. 28, 2023

(54) CONTROLLED INGROWTH FEATURE FOR ANTIMIGRATION

(71) Applicant: BOSTON SCIENTIFIC SCIMED, INC., Maple Grove, MN (US)

(72) Inventors: Colby Harris, Weston, MA (US); Stan R. Gilbert, Litchfield, NH (US); John A. Hingston, Framingham, MA (US); William Bertolino, Framingham, MA (US); Claude O. Clerc, Marlborough, MA (US); Petru Andrei, Galati (RO)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/263,353

(22) Filed: Jan. 31, 2019

(65) Prior Publication Data
US 2019/0167453 A1 Jun. 6, 2019

Related U.S. Application Data

(63) Continuation of application No. 14/873,833, filed on Oct. 2, 2015, now Pat. No. 10,219,921.
(Continued)

(51) Int. Cl.
*A61F 2/00* (2006.01)
*A61F 2/848* (2013.01)
(Continued)

(52) U.S. Cl.
CPC ............ *A61F 2/848* (2013.01); *A61F 2/0077* (2013.01); *A61F 2/07* (2013.01); *A61F 2/90* (2013.01);
(Continued)

(58) Field of Classification Search
CPC .. A61F 2/2418; A61F 2/07; A61F 2220/0075; A61F 2220/0016; A61F 2/89;
(Continued)

(56) References Cited

U.S. PATENT DOCUMENTS

| 4,994,071 A | 2/1991 | MacGregor |
| 5,591,197 A | 1/1997 | Orth et al. |

(Continued)

FOREIGN PATENT DOCUMENTS

| EP | 732088 A2 | 9/1996 |
| EP | 732089 A2 | 9/1996 |

(Continued)

*Primary Examiner* — Ann Schillinger
(74) *Attorney, Agent, or Firm* — Seager, Tufte & Wickhem, LLP

(57) ABSTRACT

A tubular prosthesis that includes a scaffolding formed by at least one scaffolding filament; a cover; and at least one controlled ingrowth feature constructed and arranged to abut an inner surface of a lumen wall when the prosthesis is implanted in the body lumen. The controlled ingrowth feature may extend inwards or outwards from the prosthesis outer surface. The controlled ingrowth feature may be formed by a scaffolding filament; by a separate filament; by the cover; and combinations thereof.

14 Claims, 20 Drawing Sheets

Related U.S. Application Data

(60) Provisional application No. 62/058,821, filed on Oct. 2, 2014.

(51) Int. Cl.
*A61F 2/07* (2013.01)
*A61F 2/90* (2013.01)
*A61F 2/915* (2013.01)
*A61F 2/88* (2006.01)
*A61F 2/89* (2013.01)

(52) U.S. Cl.
CPC ............... *A61F 2/915* (2013.01); *A61F 2/88* (2013.01); *A61F 2/89* (2013.01); *A61F 2220/0008* (2013.01); *A61F 2230/0013* (2013.01); *A61F 2230/0069* (2013.01); *A61F 2250/0026* (2013.01); *A61F 2250/0051* (2013.01)

(58) Field of Classification Search
CPC ...... A61F 2002/9665; A61F 2/06; A61F 2/90; A61F 2/962; A61F 2002/077; A61F 2220/0008; A61F 2250/0067; A61F 2002/823
See application file for complete search history.

(56) References Cited

U.S. PATENT DOCUMENTS

| | | | |
|---|---|---|---|
| 5,674,277 A | 10/1997 | Freitag | |
| 5,681,346 A | 10/1997 | Orth et al. | |
| 5,800,526 A | 9/1998 | Anderson et al. | |
| 5,814,063 A | 9/1998 | Freitag | |
| 6,027,526 A | 2/2000 | Limon et al. | |
| 6,149,681 A * | 11/2000 | Houser ................ A61F 2/90 623/1.12 |
| 6,210,429 B1 | 4/2001 | Vardi et al. | |
| 6,443,972 B1 | 9/2002 | Bosma et al. | |
| 6,506,437 B1 | 1/2003 | Harish et al. | |
| 6,709,379 B1 * | 3/2004 | Brandau ............. A61K 9/0024 600/3 |
| 6,989,071 B2 * | 1/2006 | Kocur ................ A61F 2/915 623/1.42 |
| 7,060,089 B2 | 6/2006 | Ley et al. | |
| 7,527,644 B2 | 5/2009 | Mangiardi et al. | |
| 7,547,321 B2 | 6/2009 | Silvestri et al. | |
| 7,550,003 B2 * | 6/2009 | Sogard ................ A61F 2/07 623/1.13 |
| 7,604,660 B2 | 10/2009 | Borg et al. | |
| 7,608,099 B2 | 10/2009 | Johnson et al. | |
| 7,637,934 B2 | 12/2009 | Mangiardi et al. | |
| 7,637,942 B2 | 12/2009 | Mangiardi et al. | |
| 7,651,520 B2 | 1/2010 | Fischell et al. | |
| 7,731,654 B2 | 6/2010 | Mangiardi et al. | |
| 7,785,360 B2 | 8/2010 | Freitag | |
| 7,803,180 B2 | 9/2010 | Burpee et al. | |
| 7,806,918 B2 | 10/2010 | Nissl et al. | |
| 7,815,673 B2 | 10/2010 | Bloom et al. | |
| 7,875,068 B2 | 1/2011 | Mangiardi et al. | |
| 7,887,579 B2 | 2/2011 | Mangiardi et al. | |
| 7,942,921 B2 | 5/2011 | Nissl et al. | |
| 7,959,671 B2 | 6/2011 | Mangiardi et al. | |
| 8,080,053 B2 | 12/2011 | Satasiya et al. | |
| 8,128,679 B2 | 3/2012 | Casey | |
| 8,142,488 B2 | 3/2012 | Reynolds et al. | |
| 8,206,436 B2 | 6/2012 | Mangiardi et al. | |
| 8,262,721 B2 | 9/2012 | Welborn et al. | |
| 8,267,987 B2 | 9/2012 | Johnson et al. | |
| 8,298,277 B2 | 10/2012 | Mangiardi et al. | |
| 8,323,350 B2 | 12/2012 | Nissl | |
| 8,353,946 B2 | 1/2013 | Mangiardi et al. | |
| 8,535,366 B2 | 9/2013 | Mangiardi et al. | |
| 8,652,196 B2 | 2/2014 | Nissl | |
| 8,703,168 B2 * | 4/2014 | Flanagan ............. A61F 2/91 424/424 |
| 8,834,558 B2 | 9/2014 | Nissl | |
| 8,926,683 B2 | 1/2015 | Gill et al. | |
| 10,219,921 B2 * | 3/2019 | Harris ............... A61F 2/07 |
| 2005/0131515 A1 | 6/2005 | Cully et al. | |
| 2005/0163954 A1 * | 7/2005 | Shaw ................ A61L 27/10 428/36.1 |
| 2005/0177226 A1 * | 8/2005 | Banik ................ A61L 31/16 623/1.42 |
| 2007/0005127 A1 | 1/2007 | Boekstegers et al. | |
| 2007/0112437 A1 * | 5/2007 | Shank ................ A61F 2/90 623/23.68 |
| 2007/0213810 A1 | 9/2007 | Newhauser et al. | |
| 2009/0187240 A1 | 7/2009 | Clerc et al. | |
| 2009/0248132 A1 | 10/2009 | Bloom et al. | |
| 2010/0286760 A1 | 11/2010 | Beach et al. | |
| 2011/0230957 A1 | 9/2011 | Bonsigore et al. | |
| 2012/0150277 A1 | 6/2012 | Wood et al. | |
| 2012/0310363 A1 | 12/2012 | Gill et al. | |
| 2013/0018215 A1 | 1/2013 | Snider et al. | |
| 2013/0018452 A1 | 1/2013 | Weitzner et al. | |
| 2013/0085565 A1 * | 4/2013 | Eller ................ B32B 27/322 623/1.46 |
| 2013/0103163 A1 | 4/2013 | Krimsky et al. | |
| 2013/0110253 A1 | 5/2013 | Gill et al. | |
| 2013/0116770 A1 | 5/2013 | Robinson | |
| 2013/0116771 A1 | 5/2013 | Robinson | |
| 2013/0116772 A1 | 5/2013 | Robinson | |
| 2013/0123897 A1 | 5/2013 | Robinson | |
| 2013/0172983 A1 | 7/2013 | Clerc et al. | |
| 2013/0184808 A1 | 7/2013 | Hall et al. | |
| 2013/0184810 A1 | 7/2013 | Hall et al. | |
| 2013/0325141 A1 | 12/2013 | Gill et al. | |
| 2014/0067047 A1 | 3/2014 | Eller et al. | |
| 2014/0079758 A1 | 3/2014 | Hall et al. | |
| 2014/0081414 A1 | 3/2014 | Hall et al. | |
| 2014/0086971 A1 | 3/2014 | Hall et al. | |
| 2014/0248418 A1 | 9/2014 | Eller et al. | |
| 2014/0249619 A1 | 9/2014 | Eller et al. | |
| 2014/0257461 A1 | 9/2014 | Robinson et al. | |
| 2014/0277562 A1 | 9/2014 | Seddon et al. | |
| 2014/0277573 A1 | 9/2014 | Gill et al. | |
| 2015/0073529 A1 | 3/2015 | Fleury et al. | |
| 2015/0148887 A1 | 5/2015 | Beach et al. | |

FOREIGN PATENT DOCUMENTS

| | | | | |
|---|---|---|---|---|
| EP | 1776066 B1 | 2/2012 | | |
| EP | 2702964 A1 | 4/2012 | | |
| EP | 2702964 A1 * | 3/2014 | ............... | A61F 2/07 |
| WO | 2005112821 A2 | 12/2005 | | |
| WO | 2010124286 A1 | 10/2010 | | |
| WO | 2012047308 A1 | 4/2012 | | |
| WO | 2014010679 A1 | 1/2014 | | |
| WO | WO-2014010679 A1 * | 1/2014 | ............... | A61F 2/07 |

* cited by examiner

CONTROLLED INGROWTH FEATURE FOR ANTIMIGRATION

CROSS-REFERENCE TO RELATED APPLICATIONS

This application is a continuation of U.S. application Ser. No. 14/873,833, filed Oct. 2, 2015, which claims priority under 35 U.S.C. § 119 to U.S. Provisional Application Ser. No. 62/058,821, filed Oct. 2, 2014, the entirety of which is incorporated herein by reference.

BACKGROUND

Stents may be implanted in a variety of body lumens or vessels such as within the vascular system, urinary tracts, gastrointestinal tracts, fallopian tubes, coronary vessels, secondary vessels, airways, structural heart (valve frame), etc. They may be self-expanding, expanded by an internal radial force, such as when mounted on a balloon, or a combination of self-expanding and balloon expandable (hybrid expandable). Some stents are partially or fully covered. Migration of the stent from its initial site of implantation can be undesirable.

Without limiting the scope of the invention a brief summary of some of the claimed embodiments of the disclosure is set forth below. Additional details of the summarized embodiments of the disclosure and/or additional embodiments of the disclosure may be found in the Detailed Description of the Invention below.

BRIEF SUMMARY

A prosthesis for controlled tissue ingrowth may comprise a scaffolding extending from a first prosthesis end to a second prosthesis end; a cover; and a controlled tissue ingrowth feature constructed and arranged to abut an inner surface of a lumen wall when the prosthesis is implanted in the body lumen, the controlled ingrowth feature selected from the group consisting of protruding elements and dimples; wherein the controlled ingrowth feature is formed by a scaffolding filament; by a separate filament; by the cover; and combinations thereof.

The prosthesis may be a fully covered prosthesis. The prosthesis has a first prosthesis end and a second prosthesis end. The prosthesis may have a longitudinal length measured from the first prosthesis end to the second prosthesis end of about 40 mm to about 400 mm, preferably about 60 mm to about 200 mm.

The scaffolding may be selected from the group consisting of: a mesh; a plurality of spaced apart rings; laser cut from a tube; and laser cut from a sheet of material formed into a tube. The scaffolding may be a single layer. The scaffolding may extend from a first prosthesis end to a second prosthesis end. The scaffolding has a scaffolding outer surface. The scaffolding may have a longitudinal length of about 40 mm to about 400 mm, preferably about 60 mm to about 200 mm. The scaffolding defines a plurality of scaffolding openings. The scaffolding openings may have a size of about 1×1 mm to about 5×5 mm.

The scaffolding may be formed by a scaffolding filament. The scaffolding filament may have a diameter of 0.06 mm to 0.60 mm. The scaffolding filament may be bioabsorbable. The scaffolding filament may comprise nitinol, polyethylene terephthalate (PET), or a bioabsorbable material.

The scaffolding may be a mesh. The mesh may be an interwoven mesh. The scaffolding filament may be interwoven at a uniform angle to form the mesh. The interwoven mesh has a plurality of scaffolding filament crossings.

The cover may be non-porous. The cover may be attached to the scaffolding outer surface. The cover may have a length equal to the longitudinal length of the scaffolding. The cover may form the prosthesis outer surface. The cover may have a thickness of about 10 μm to about 400 μm, preferably about 50 μm to about 200 μm, more preferably 100 μm to about 150 μm, most preferably about 100 μm. The cover may have a variable thickness or a uniform thickness.

The controlled ingrowth feature may form a maximum of about 30% of an outer surface area of the prosthesis. The controlled ingrowth feature may be positioned about 5 mm to about 25 mm from the closest prosthesis end; preferably about 10 mm to about 20 mm from the closest prosthesis end; more preferably about 12 mm to about 15 mm from the closest prosthesis end; and most preferably about 15 mm from the closest prosthesis end. The controlled ingrowth feature may be constructed and arranged to abut an inner surface of the lumen wall when the prosthesis is implanted in a body lumen. The controlled ingrowth feature may be constructed and arranged not penetrate the lumen wall when the prosthesis is implanted in a body lumen.

The controlled ingrowth feature may be a protruding element. The protruding element may be selected from the group consisting of a protruding scaffolding filament section; a separate filament attached to the scaffolding; a protruding mesh region; and a protruding ring turn. The protruding element is positioned above the scaffolding. The protruding element may define a gap with a gap height of about 0.25 mm to about 4.0 mm, preferably about 0.25 to about 2 mm. The gap may be an open gap or a closed gap. The prosthesis may have only open gaps; only closed gaps; or a combination of open gaps and closed gaps.

The protruding element may be a plurality of protruding elements.

The protruding scaffolding filament section may form about 2.5% to about 20% of the outer surface area of the prosthesis. The protruding scaffolding filament section may extend between two scaffolding filament crossings immediately adjacent one another, or may extend over a scaffolding filament crossing. The protruding scaffolding filament section has a first end and a second end. The first and second ends of the protruding scaffolding filament section may be separated by a distance of 1.5 mm to 7.5 mm. The protruding scaffolding filament section may have a rounded shape, a square shape, or a triangular shape. The protruding scaffolding filament section may have no sharp bends. The protruding scaffolding filament section may have a rounded shape. The protruding scaffolding filament section may be oriented at a non-parallel angle to a longitudinal axis of the prosthesis.

The separate filament may form about 2.5% to about 20% of the outer surface area of the prosthesis. The separate filament may extend between two scaffolding filament crossings immediately adjacent one another, or may extend over a scaffolding filament crossing. The separate filament has a first end and a second end. The first and second ends of the separate filament may be separated by a distance of 1.5 mm to 7.5 mm. The separate filament may have a rounded shape, a square shape, or a triangular shape. The separate filament may have no sharp bends. The separate filament may have a rounded shape. The separate filament may be oriented at a non-parallel angle to a longitudinal axis of the prosthesis.

The protruding mesh region may define an open gap with a maximum gap height of 0.50 mm to 2 mm. The protruding mesh region has a first edge and a second edge. The first and second edges may be separated by a longitudinal distance of 2 mm to 10 mm. The protruding mesh region may form about 2.5% to about 20% of the outer surface area of the prosthesis.

The ring may be formed by a scaffolding filament. Each ring has interconnected ring turns. The ring turns include first ring turns forming the first ring end and second ring turns forming the second ring end. The rings may include a first ring with a variable diameter and a second ring with a uniform diameter. The first ring has a first ring end with a first diameter and a second ring end with a second diameter greater than the first diameter, wherein the second ring end is the protruding element. The second ring end may be positioned above the cover and define a gap therebetween. About 25-75% of the longitudinal length of the first ring, as measured from the first and second ring ends, may be positioned above the outer surface of the cover. The gap may have a maximum gap height of 0.25 mm to 4 mm.

The first ring may either have a truncated cone shape with a single uniform slope or angle β; or a cylindrical section with a uniform diameter and a truncated cone section with a single uniform slope or angle β extending from the cylindrical section.

The prosthesis may include a second ring with a first end having a first diameter and a second end having the first diameter. The prosthesis may have only first rings. The prosthesis may have first and second rings. The rings may be interconnected only by the cover.

The controlled ingrowth feature may be a dimple. The prosthesis may have a single dimple or a plurality of dimples. The dimple may be selected from the group consisting of a dimple cover section of the cover; a reinforced dimple comprising a dimple cover section and a section of the scaffolding; a dimple patch; and combinations thereof.

The prosthesis with a dimple may have a single layer of scaffolding, or two layers of scaffolding with only one of the two layers of scaffolding extending from the first prosthesis end to the second prosthesis end. The second layer of scaffolding is a scaffolding patch.

The dimple may span a single scaffolding opening or a plurality of scaffolding openings. The dimple may span a scaffolding opening having a larger size than the other scaffolding openings. The dimple may define a dimple gap with a maximum gap height of about 3 mm. The dimple may have a maximum longitudinal extent of 1 mm to 10 mm. The maximum longitudinal extent of the dimple may be less than the longitudinal length of the prosthesis. The dimple may have a maximum circumferential extent of 1 mm to 10 mm. The maximum circumferential extent may be equal to or less than the circumference of the prosthesis.

The cover may comprise a non-dimple cover section and a dimple cover section. The dimple cover section may be entirely surrounded by the non-dimple cover section. The dimple cover section may form a dimple gap. The dimple gap may have a gap height of about 0.25 mm to about 2.0 mm. The dimple may define a single dimple gap or a plurality of dimple gaps.

The dimple is sized so as not to exert a suction force on the lumen wall when the prosthesis is implanted. The dimple may have a longitudinal extent of about 1 mm to about 10 mm; a circumferential extent of about 1 mm to about 10 mm; an area of about 1 $mm^2$ to 100 $mm^2$, preferably 5 $mm^2$ to about 50 $mm^2$, and most preferably 25 $mm^2$; and combinations thereof. The dimple may form about 1% to about 30% of the outer surface area of the prosthesis, preferably 5% to 20% of the outer surface area of the prosthesis, and most preferably 10% of the outer surface area of the prosthesis.

Scaffolding may extend over the dimple gap. The scaffolding extending over the dimple gap may be either a portion of the scaffolding or a scaffolding patch attached to the prosthesis outer surface. A portion of the mesh scaffolding may extend over the dimple gap.

A scaffolding patch may extend over the dimple gap and be secured to the non-dimple cover section.

The dimple gap may span a scaffolding opening having a larger size than other scaffolding openings.

These and other aspects of a prosthesis of the present disclosure are pointed out with particularity in the detailed description and the claims annexed hereto and forming a part hereof. However, for further understanding of the invention reference can be made to the drawings which form a further part hereof and the accompanying descriptive matter, in which there is illustrated and described embodiments of the invention.

BRIEF DESCRIPTION OF THE DRAWINGS

A detailed description of the invention is hereafter described with specific reference being made to the drawings.

DETAILED DESCRIPTION

Figure 1:
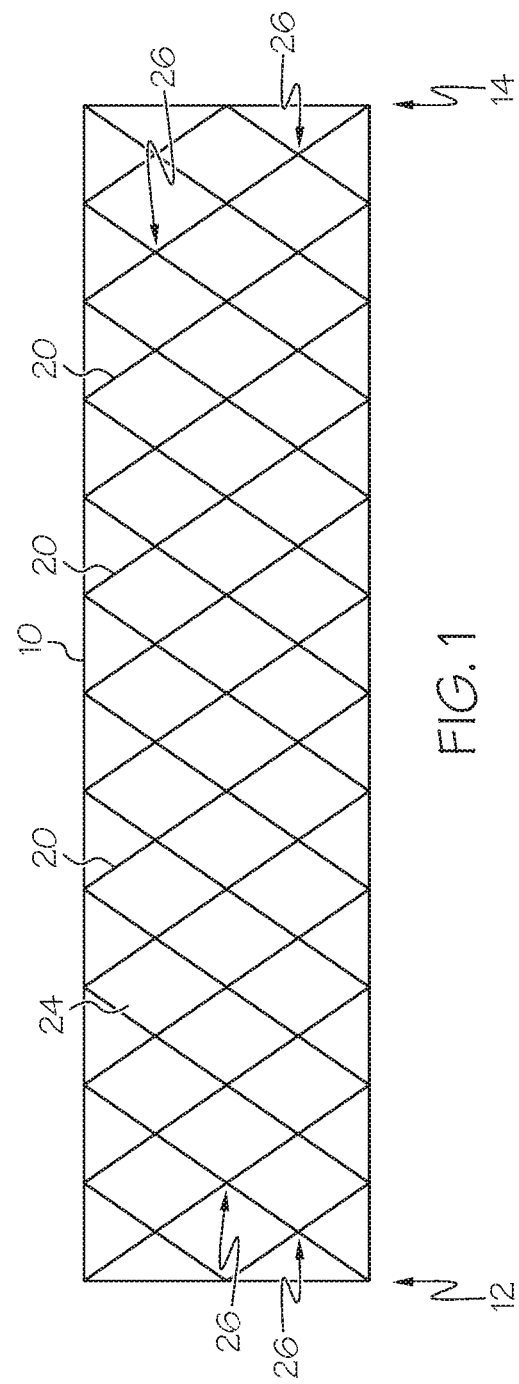
FIG. 1 is a flat view of an exemplary interwoven prosthesis.

While this disclosure may be embodied in many different forms, there are described in detail herein specific embodiments of the disclosure. This description is an exemplification of the principles of the disclosure and is not intended to limit the disclosure to the particular embodiments illustrated.

For the purposes of this disclosure, like reference numerals in the figures shall refer to like features unless otherwise indicated.

As used in this disclosure, the terms "connect" or "engage" do not include "indirect" connection or engagement.

As used in this disclosure, "thickness" is measured radially from the prosthesis outer surface 16 to the prosthesis inner surface 17; "width" is measured in a circumferential direction; and "length is measured in a longitudinal direction.

As used in this disclosure, an "end" is the last part or extremity of an element, while an "end region" is a region adjacent to, and includes, the "end."

Prosthesis

A tubular prosthesis or stent 10 as described herein provides for controlled tissue ingrowth (see e.g. FIGS. 1-13B and 15A-21C). Thus, the prosthesis 10 may be described as a "controlled tissue ingrowth prosthesis". "Controlled tissue ingrowth" as used herein means that the prosthesis is constructed and arranged for a pre-determined amount of tissue ingrowth when the prosthesis 10 is implanted.

The prosthesis 10 includes a first prosthesis end 12; a second prosthesis end 14; a prosthesis outer surface 16; a prosthesis inner surface 17 opposite the prosthesis outer surface 16, the prosthesis inner surface 17 defining the prosthesis lumen; a scaffolding 18; a cover 60 and a controlled ingrowth feature 40. The pre-determined amount of tissue ingrowth depends in part on the cover 60 and in part on the controlled ingrowth feature 40.

Figure 2:
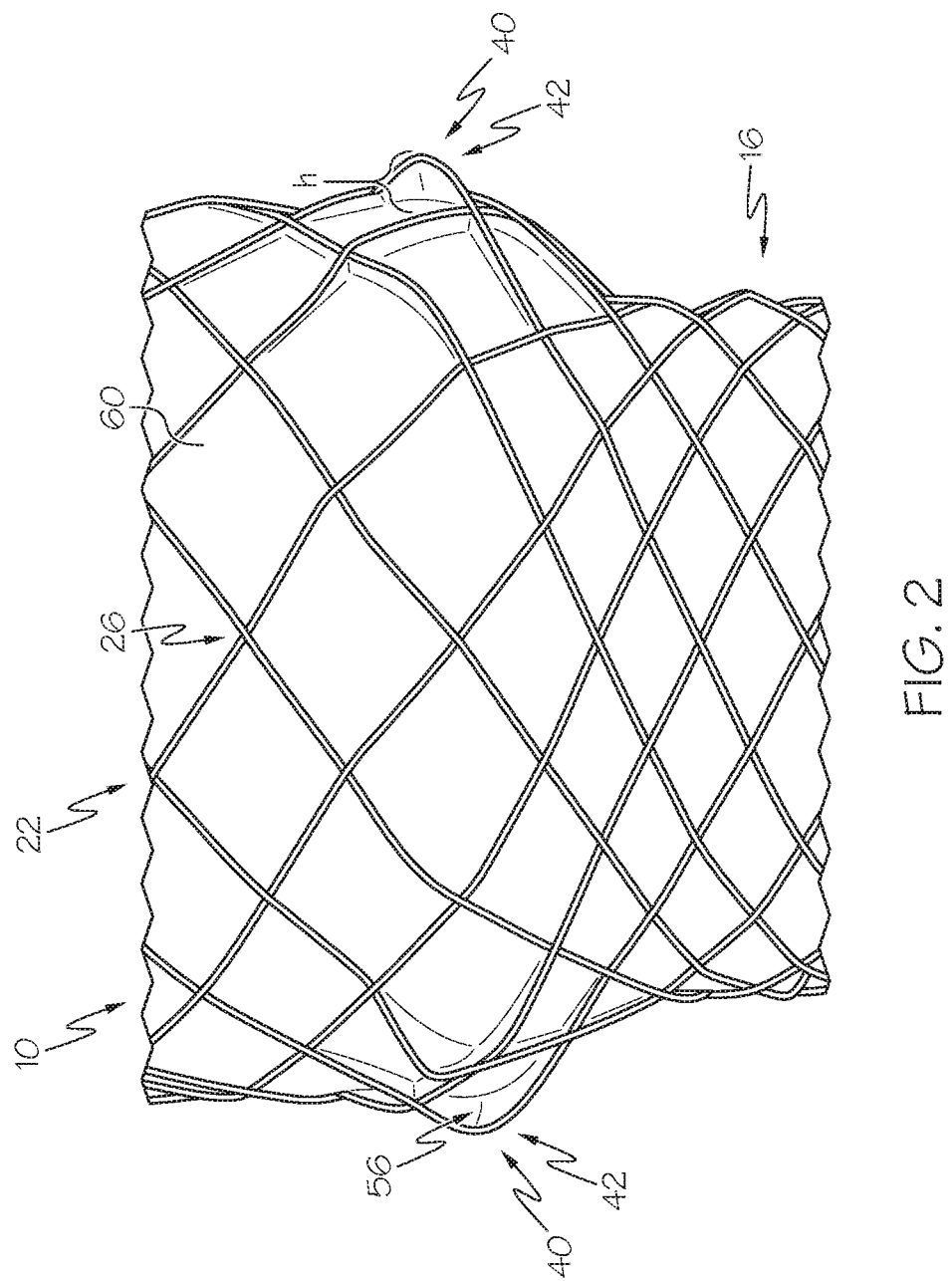
FIG. 2 is a view of a portion of an exemplary prosthesis with a raised filament section.
Figure 3:
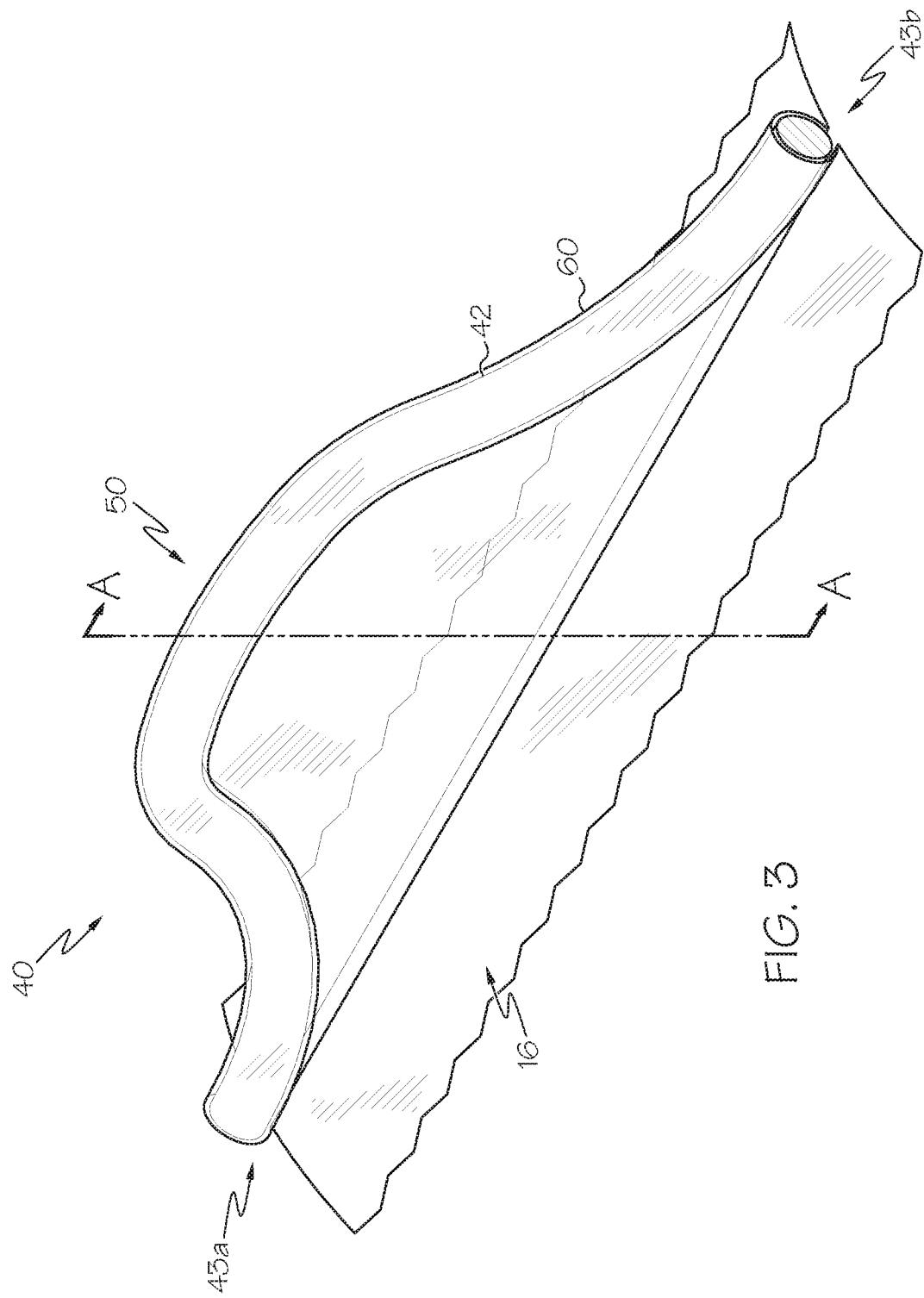
FIG. 3 is a perspective view a raised filament section with a closed gap.
Figure 16A:
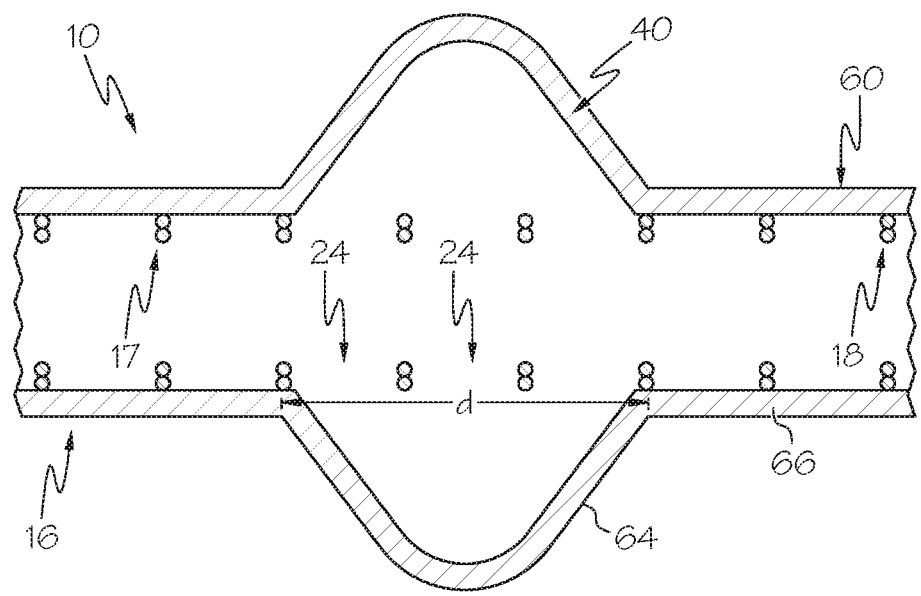
FIGS. 16A-20 are schematic partial cross-sectional views of a dimple.
Figure 16B:
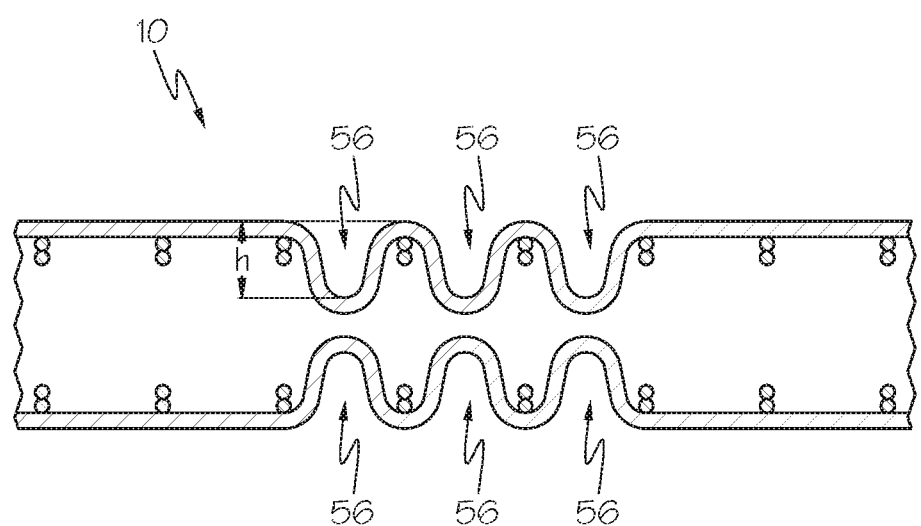
Figure 17:
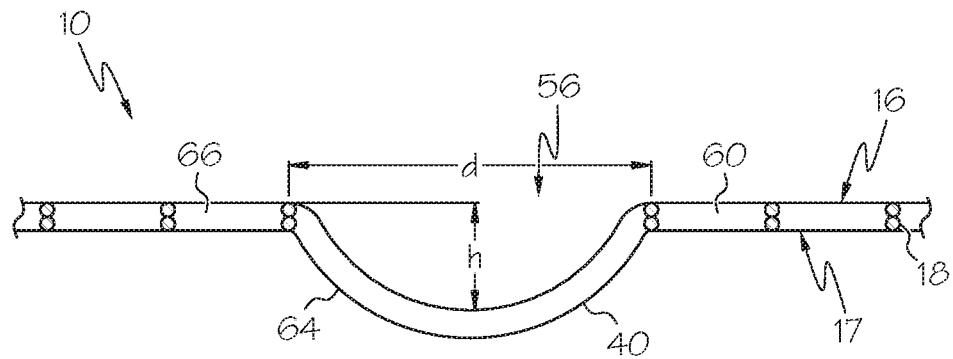
Figure 18:
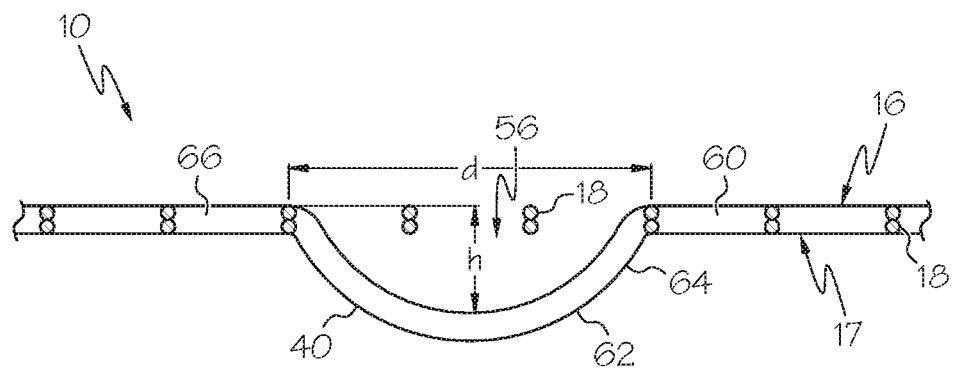

The prosthesis outer surface 16 may be defined by the cover 60 and the controlled ingrowth feature 40 (see e.g. FIG. 9), or entirely by the cover 60 (see e.g. FIGS. 2 and 16B). The prosthesis outer surface 16 has an outer surface area. The prosthesis inner surface 17 may be defined by the cover 60 and by the scaffolding 18 (see e.g. FIGS. 2, 9, and 16B). The prosthesis inner surface 17 has an inner surface area.

The prosthesis 10 is expandable from a compressed delivery diameter to an expanded implanted diameter. As is known in the art the prosthesis 10 may self-expand from the compressed delivery diameter to the expanded implanted diameter, or may be expanded by a balloon from the compressed delivery diameter to the expanded implanted diameter. For this disclosure, a "diameter" of the prosthesis 10 does not take into account the overall height of the controlled ingrowth feature 40. In other words the diameter of the prosthesis is based on the diameter measured from the outer surface of the cover 60. As used in this disclosure, "diameter" is the distance of a straight line extending between two points and does not indicate a particular cross-sectional shape.

Figure 10:
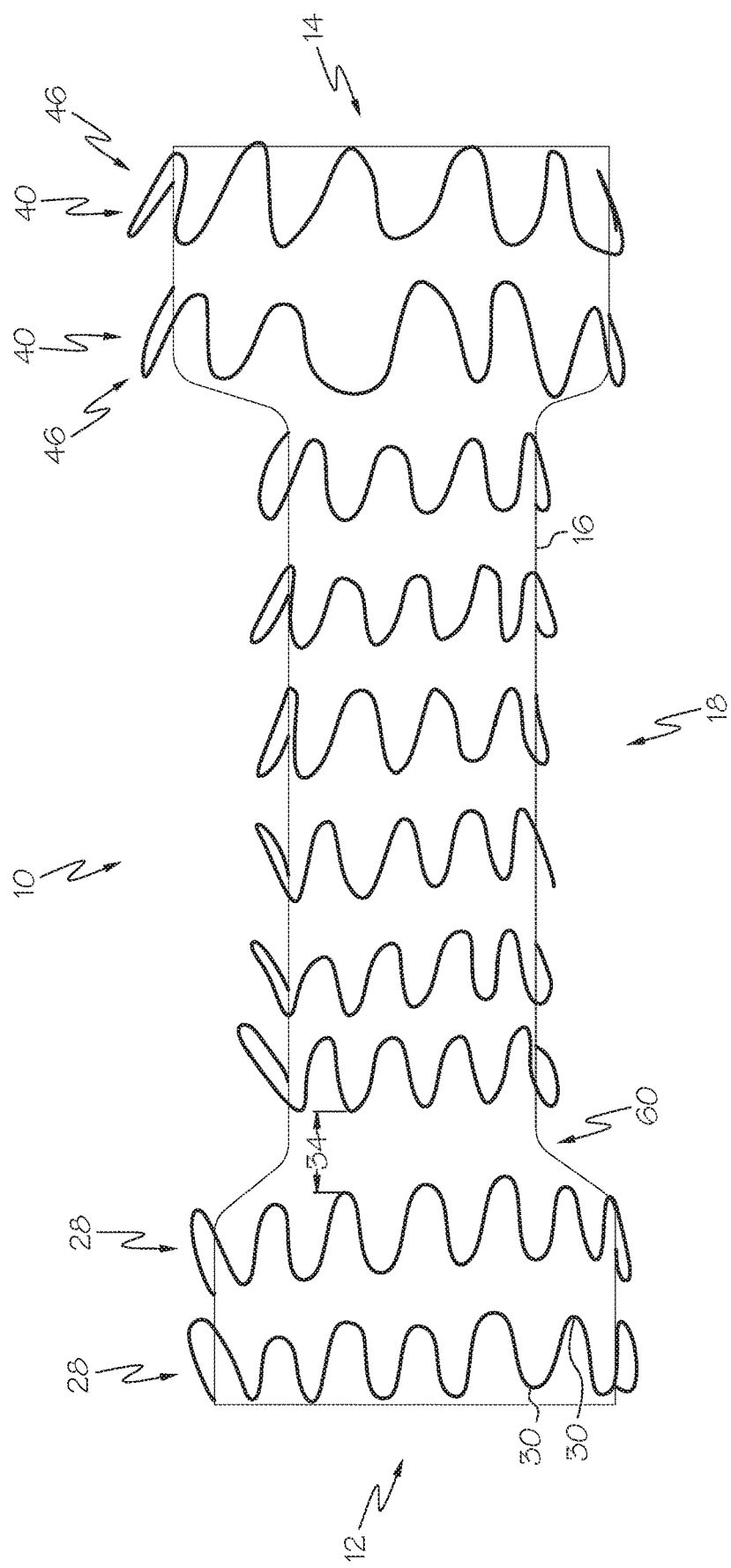
FIG. 10 is a view of an exemplary prosthesis with protruding ring turns.
Figure 11:
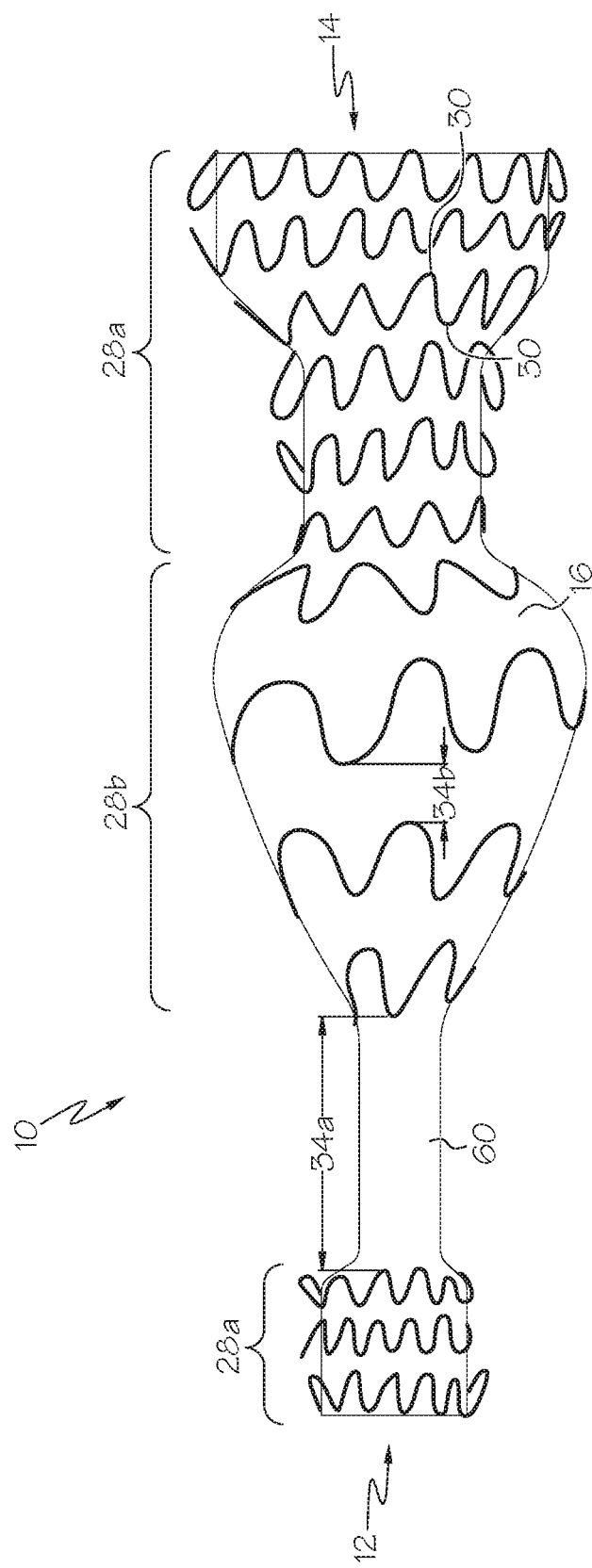
FIG. 11 is a view of another exemplary prosthesis with protruding ring turns.
Figure 19:
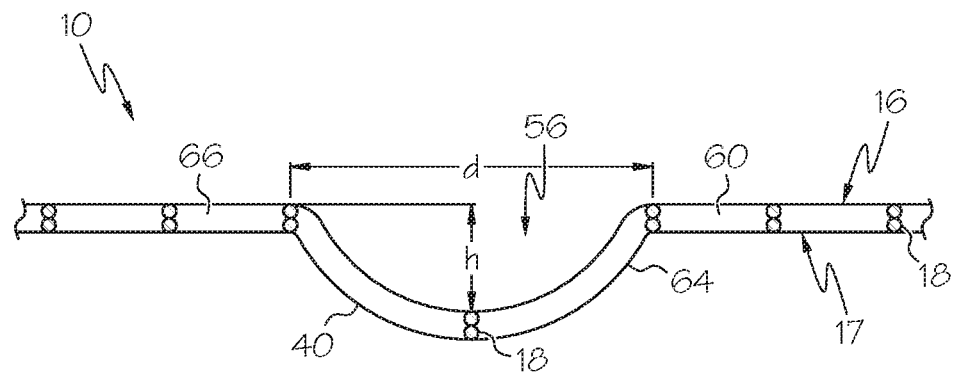

A prosthesis 10 as described herein may have a substantially constant diameter (see e.g. FIGS. 9 and 15A-18); prosthesis end regions with a greater diameter than the prosthesis middle region (see e.g. FIGS. 2 and 10); or a variable diameter (see e.g. FIGS. 11 and 19). The prosthesis 10 may have a minimum diameter of about 15 mm and a maximum diameter of about 40 mm. The prosthesis end regions may have a diameter of about 15 mm to about 35 mm, while the prosthesis middle region may have a diameter of about 15 mm to about 25 mm.

The prosthesis 10 may have a longitudinal length measured from the first prosthesis end 12 to the second prosthesis end 14 of about 40 mm to about 400 mm, preferably about 60 mm to about 200 mm.

The prosthesis 10 can be implanted in any suitable body lumen including the gastrointestinal system (e.g. colon, esophagus), the hepatobiliary system (e.g. biliary tract), the respiratory system (e.g. trachea), the cardiovascular system, and elsewhere in the body.

A. Scaffolding

The prosthesis 10 has a tubular scaffolding 18 that extends from the first prosthesis end 12 to the second prosthesis end 14. The scaffolding 18 has a scaffolding outer surface, a scaffolding inner surface, and a thickness measured from the scaffolding outer surface to the scaffolding inner surface. The scaffolding 18 may have a longitudinal length of about 40 mm to about 400 mm, preferably about 60 mm to about 200 mm; a thickness of about 0.06 mm to about 0.60 mm; and combinations thereof. The scaffolding 18 defines a plurality of scaffolding openings 24 (see e.g. FIGS. 1-2, 9, and 15A-22). The scaffolding openings 24 may have a size of about 1×1 mm to about 5×5 mm.

The scaffolding 18 may be in the form of a mesh 22 (see e.g. FIGS. 1-2, 9, and 14-20C); a plurality of longitudinally spaced apart rings 28 (see e.g. FIGS. 10-11); laser cut from a tube; or laser cut from a sheet of material that is welded to form a tube.

Figure 20:
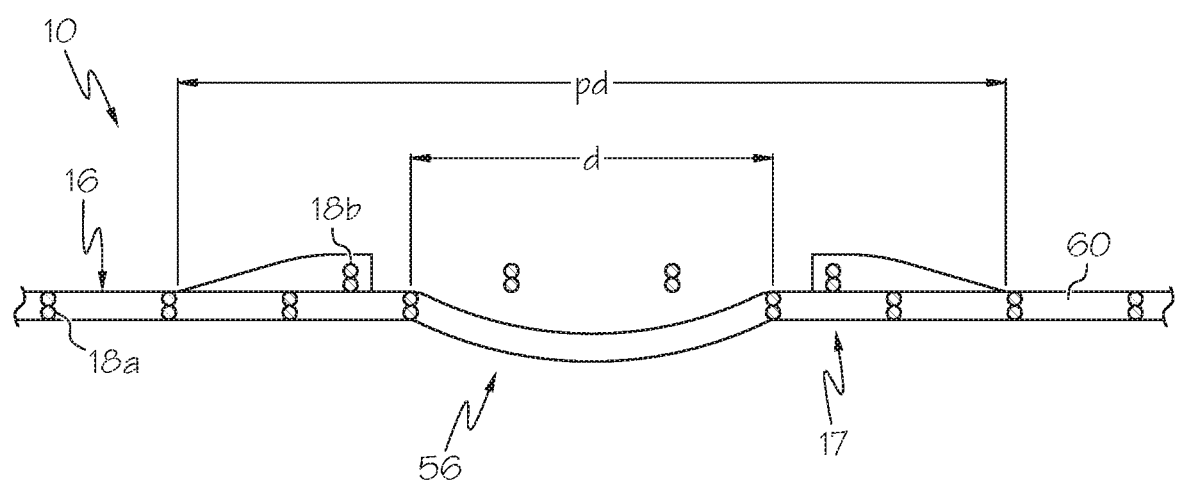

The prosthesis 10 may have a single layer of scaffolding 18 (e.g. FIGS. 2-13B, 15A-19, and 21A-22), or two layers of scaffolding 18 (e.g. FIG. 20). As discussed below in greater detail, where the prosthesis 10 has two layers of scaffolding, only one layer of scaffolding 18 extends from the first prosthesis end 12 to the second prosthesis end 14.

The scaffolding 18 is expandable from a compressed delivery diameter to an expanded implanted diameter. Suitable materials for the scaffolding 18 are provided below. The structures forming the scaffolding 18 may have any suitable cross-sectional shape, for example but not limited to a round cross-sectional shape (see e.g. FIG. 3), or a rectangular cross-sectional shape (not shown). A scaffolding structure, e.g. a scaffolding filament 20, may have a diameter of about 0.06 mm to about 0.60 mm. The scaffolding filament 20 can be a monofilament or a multifilament.

A "mesh" 22 as used in the present disclosure has at least one scaffolding filament 20; a plurality of scaffolding filament crossings 26; defines a plurality of scaffolding openings 24; and may be formed by any suitable method, including but not limited to braiding, weaving, and knitting. A prosthesis 10 with a mesh scaffolding may be described as an interwoven prosthesis. A scaffolding filament 20 forming the mesh scaffolding 22 may have a length equal to or greater than the longitudinal length of the mesh scaffolding 22.

A "ring" 28 as used in the present disclosure extends around the entire circumference of the prosthesis 10; and has a plurality of interconnected ring turns 30, with some ring turns 30 facing the first prosthesis end 12, and other ring turns 30 facing the second prosthesis end 14 (see e.g. FIGS. 10-11). A ring 28 may be formed by a scaffolding filament 20. Thus the scaffolding filament 20 has sections forming the ring turns 30 and sections 32 interconnecting the ring turns 30. Sections 32 extending between, and connecting, two ring turns 30 may be straight or include at least one bend. The scaffolding filaments 20 forming the rings 28 of a prosthesis 10 may have the same diameter or different diameters.

The ring 28 has a longitudinal length measured from the first and second ring ends of about 1 mm to about 30 mm, preferably about 5 mm to about 15 mm, most preferably about 10 mm. A prosthesis 10 may have rings 28 with different longitudinal lengths or rings 28 with the same longitudinal length.

A prosthesis 10 formed of rings 28 has at least two rings 28 connected to one another only by the cover 60 (see e.g. FIGS. 10-11).

A prosthesis 10 may have rings 28 formed of the same material or rings 28 formed of different materials.

A prosthesis 10 may have rings 28 with the same radial strength or rings 28 of different radial strengths.

A prosthesis 10 may have rings 28 with the same diameter (see e.g. the rings forming middle section of the prosthesis 10 shown in FIG. 10), or rings with different diameters (see e.g. FIGS. 10-11).

The rings 28 of a prosthesis 10 may be separated by a substantially constant longitudinal distance 34 (see e.g. FIG. 10) or by different longitudinal distances 34 (see e.g. 34a and 34b of FIG. 11). The longitudinal distance 34 between adjacent rings 28 may be about 0 mm to about 50 mm. Where the longitudinal distance is about 0 mm, the rings are in phase and the proximal turns of one ring and the distal turns of the adjacent ring are aligned on a line perpendicular to the longitudinal axis of the prosthesis.

As is known in the art, scaffolding that is formed by laser cutting a tube or a sheet of material typically has a plurality of interconnected struts that defines a plurality of scaffolding openings. The interconnected struts may be arranged in any pattern.

B. Cover

As discussed above, the pre-determined amount of tissue ingrowth depends in part on the cover 60. The cover 60 is constructed and arranged to prevent tissue from growing through the scaffolding openings 24 and into the lumen of the prosthesis 10. Examples of suitable materials for the cover 60 are provided below.

To prevent tissue from growing into the lumen of the prosthesis 10, the prosthesis 10 is a fully covered prosthesis. As used in this disclosure, a "fully covered prosthesis" has a cover 60 that extends over the scaffolding outer surface at least from the first prosthesis end 12 to the second prosthesis end 14 and occludes the scaffolding openings 24. Therefore, the cover 60 has a length equal to, or greater than, the longitudinal length of the prosthesis 10. About 80% of the cover 60 may be supported by and/or secured to the scaffolding 18. The prosthesis 10 may further include a cover extending over the inner surface of the scaffolding 18.

The cover 60 may be non-porous. Alternatively, the cover 60 may be porous. For example if the cover 60 is porous, the pore size and/or pores location may be constructed and arranged so that there is no tissue growth through the cover 60 and into the lumen of the prosthesis 10; the inner surface of the cover 60 may have a impermeable layer the prevents tissue growth therethrough; and combinations thereof.

The cover 60 may have a thickness of about 10 µm to about 400 µm, preferably about 50 µm to about 200 µm, more preferably 100 µm to about 150 µm, most preferably about 100 µm. The cover 60 may have a variable thickness (see e.g. FIG. 22) or a uniform thickness (see e.g. FIG. 17). Although the cover 60 typically has a thickness less than the diameter of the scaffolding filament 20, the cover 60 may have a thickness equal to or greater than the diameter of the scaffolding filament 20. Where the cover 60 has a thickness greater than the diameter of the scaffolding filament 20 the cover 60 extends over the outer surface of the scaffolding 18. Where the cover has a thickness less than the diameter of the scaffolding filament 20, the scaffolding filament 20 may protrude slightly outward from outer surface of the cover 60. The height of the slight outward protrusion of the scaffolding filament 20 is minimal (e.g. a height of about 0.5 mm). Thus, the prosthesis outer surface 16 is substantially uniform.

C. Controlled Ingrowth Feature

As discussed above, the pre-determined amount of tissue ingrowth when the prosthesis 10 is implanted depends in part on the controlled ingrowth feature 40. Some features of the controlled ingrowth feature that affect the pre-determined amount of tissue ingrowth include the amount of the prosthesis outer surface 16 that is formed by the controlled ingrowth feature 40; the gap height h and overall height of the controlled ingrowth feature; and combinations thereof.

As discussed below in greater detail, the controlled ingrowth feature 40 may form a maximum of about 30% of the prosthesis outer surface 16.

Each controlled ingrowth feature 40 defines a gap 56 between the controlled ingrowth feature 40 and the prosthesis outer surface 16. The gap 56 has a maximum extent or height h measured from the prosthesis outer surface 16 (hereinafter "gap height h"; see e.g. FIGS. 2, 4, 8A-C, 9, 13A, and 16B-19). Depending on the type of controlled ingrowth feature 40, the controlled ingrowth feature 40 may have maximum gap height h of about 0.25 mm to about 4 mm, or about 0.5 mm to about 2 mm.

The controlled ingrowth feature 40 is positioned between the first and second prosthesis ends 12, 14, and may be parallel, or non-parallel, to the longitudinal axis of the prosthesis 10. Exemplary configurations of the placement of the controlled ingrowth feature(s) 40 along the longitudinal length of the prosthesis 10 are shown in FIGS. 2, 9-11, 14, and 22A-E. A longitudinal distance separates the controlled ingrowth feature 40 from each prosthesis end 12, 14. In other words, a section of the prosthesis 10 separates the controlled ingrowth feature 40 and the closest prosthesis end 12, 14. The controlled ingrowth feature may be positioned about 5 mm to about 25 mm from the closest prosthesis end 12,14; preferably about 10 mm to about 20 mm from the closest prosthesis end 12,14; more preferably about 12 mm to about 15 mm from the closest prosthesis end 12,14; and most preferably about 15 mm from the closest prosthesis end 12,14. For example, as shown in FIG. 2, the closest prosthesis end to the controlled ingrowth feature 40 is a distance beyond the top edge of the figure and the end of the controlled ingrowth feature 40 closest to the top edge of the figure is a distance from that closest prosthesis end. Without being bound by theory, having a longitudinal distance separating an end or edge of a controlled ingrowth feature 40 from the closest prosthesis end 12, 14 mitigates granulation tissue formation at or near the prosthesis end 12, 14 when the prosthesis 10 is implanted in a body lumen.

Forming the controlled ingrowth feature 40 is part of the method of forming the prosthesis 10 so that, once formation of the prosthesis 10 is completed, the prosthesis 10 has a controlled ingrowth feature 40. In other words, the prosthesis has a controlled ingrowth feature 40 at all times and the presence of the controlled ingrowth feature is not dependent on the prosthesis being in a particular state, e.g. a compressed delivery state or an expanded deployed state.

A controlled ingrowth feature 40 may extend outwardly from the prosthesis outer surface 16 of the prosthesis 10 (see e.g. FIGS. 2-11), or may extend inwardly from the prosthesis outer surface 16 (see e.g. FIGS. 14-19). The controlled ingrowth feature 40 may be formed by a scaffolding filament 20; by a separate filament 48; by the cover 60, and combinations thereof.

C.1. Outwardly Extending Controlled Ingrowth Feature/Protruding Element

As discussed above, the controlled ingrowth feature 40 may extend outwardly. A controlled ingrowth feature 40 that extends outwardly can be described as an outwardly extending controlled ingrowth feature or as a protruding element (hereinafter "protruding element"). Thus, as used in this disclosure, a "protruding element" extends outwardly and has a first end/edge and a second end/edge positioned at the outer surface of the cover 60.

A prosthesis 10 with a protruding element 40 has a single layer of scaffolding 18 (see e.g. FIGS. 2-13B). The protruding element 40 may be formed by a part of the scaffolding 18 (see e.g. FIGS. 2 and 9-11), or by a separate filament 48 incorporated into the scaffolding 18 (see e.g. FIG. 6). Examples of a part of the scaffolding 18 forming a protruding element 40 include: a section of a scaffolding filament 20 forming the mesh 22 (see e.g. FIG. 2; referred hereinafter as a protruding scaffolding filament section 42); a region of the mesh 22 (see e.g. FIG. 9; referred hereinafter as a protruding mesh region 44); and a ring turn 30 that protrudes (see e.g. FIGS. 10-11; referred hereinafter as a protruding ring turn 46).

As discussed above, the pre-determined amount of tissue ingrowth depends in part on the amount of the prosthesis outer surface that is formed by the protruding element 40. For protruding elements 40 that are a part of the scaffolding 18, a separate filament 48 incorporated into the scaffolding, or a protruding scaffolding filament section 42, a maximum of about 20% of the prosthesis outer surface 16 is formed by the protruding elements 40 (see e.g. FIGS. 2-9). Thus for these embodiments, about 80% of the cover is supported by and/or secured to the scaffolding 18. These types of protruding elements 40 may form about 2.5% to about 20% of the prosthesis outer surface 16. Without being bound by theory, having a maximum of about 20% of the prosthesis outer surface 16 with protruding elements 40 may maintain adhesion between the cover 60 and the scaffolding 18, thereby preventing tissue ingrowth through the scaffolding 18; may prevent the cover 60 from being pulled away from the scaffolding 18 by tissue ingrowth; may prevent collapse of the cover 60 into the lumen of the prosthesis; and combinations thereof.

For protruding elements 40 that are protruding ring turns 46, a maximum of about 75% of the prosthesis outer surface 16 is formed by the protruding elements 40. As discussed below in greater detail, this type of protruding element 40 may form about 25% to about 75% of the prosthesis outer surface 16.

The pre-determined amount of tissue ingrowth depends in part on the gap height h of the protruding element 40 and the overall height of the protruding element 40. The gap height h is measured from the prosthesis outer surface 16 to the protruding element 40. The gap height h does not include the diameter of the protruding element 40. The combination of the gap height h and the diameter of the protruding element 40 is a measure of the overall height of the protruding element 40.

The overall height of the protruding element 40 is constructed and arranged so that the protruding element 40 does not puncture or jab into the lumen wall after the prosthesis 10 is implanted in a body lumen. In other words, when the prosthesis 10 is implanted the protruding element 40 abuts/contacts the lumen wall 80 but does not penetrate the lumen wall 80. The contact of the protruding element 40 against the lumen wall irritates the tissue of the lumen wall 80, which induces tissue growth around the protruding element 40 (see e.g. FIGS. 4-5 and 7).

The gap height h and the overall height are substantially fixed because the protruding element 40 has limited flex. Because the protruding element 40 has limited flex, the gap height h and the overall height of the protruding element 40 is substantially uniform. In other words, because the movement of the protruding element 40 up or down relative to the cover 60 is minimized, the protruding element 40 has a substantially uniform gap height h and a substantially uniform overall height. A prosthesis 10 with protruding elements 40 with a uniform gap height h and overall height has controlled tissue ingrowth. In contrast, a prosthesis with outwardly extending features that flex up or down relative to a covering would have uncontrolled tissue ingrowth. For protruding elements 40 that are a part of the scaffolding 18, a separate filament 48 incorporated into the scaffolding, or a protruding scaffolding filament section 42, the gap height h and the overall height are substantially fixed because the protruding element 40 has a preset curvature that limits flex of the protruding element 40.

Depending on the configuration of the protruding element 40, the gap height may be uniform or variable (see e.g. FIGS. 8-11). Where the gap height h is variable, the gap height h is the maximum gap height h. Depending on the type of protruding element 40, the maximum gap height h may be about 0.25 mm to about 4 mm, or about 0.50 mm to about 2 mm.

As discussed above, prosthesis outer surface 16 is considered to be substantially uniform even though the scaffolding filament 20 may protrude slightly from the outer surface of the cover 60. Thus, the height of the outward protrusion from the outer surface of the cover 60 is not considered for the purpose of measuring the gap height h and the overall height of a protruding element 40.

The protruding element 40 may have a diameter of about 0.06 mm to about 0.6 mm. Thus, the overall height of the protruding element may be about 0.56 mm to about 2.6 mm. The overall height of the protruding element 40 may be described with reference to the diameter of the protruding element 40. The overall height of the protruding element 40 may be about 4× to about 9× the diameter of the protruding element 40. For example, where the protruding element 40 has a diameter of 0.06 mm and an overall height of 0.56 mm the overall height is about 9.3 times the diameter of the protruding element 40. Similarly, where the protruding element 40 has a diameter of 0.6 mm and an overall height of 2.6 mm, the overall height is about 4.33 times the diameter of the protruding element 40.

The gap height h and overall height of the protruding element 40 may depend on the intended implantation site. For example when the prosthesis 10 is constructed for implantation in the esophagus, the overall height of the protruding element 40 is between about 0.1 mm and about 2 mm because the lumen wall in the esophagus varies from 1.5 mm to 4 mm, depending on location and state of swallowing. The range for the overall height allows for tissue growth around the protruding element 40 without a risk of eroding completely through the lumen wall of the esophagus. Where the prosthesis 10 is constructed for implantation in anatomy further down the gastrointestinal tract, such as the large and small bowel, the protruding element 40 may have a smaller overall height, between about 0.5 mm and about 1 mm, as the lumen wall is thinner in these regions.

Figure 4:
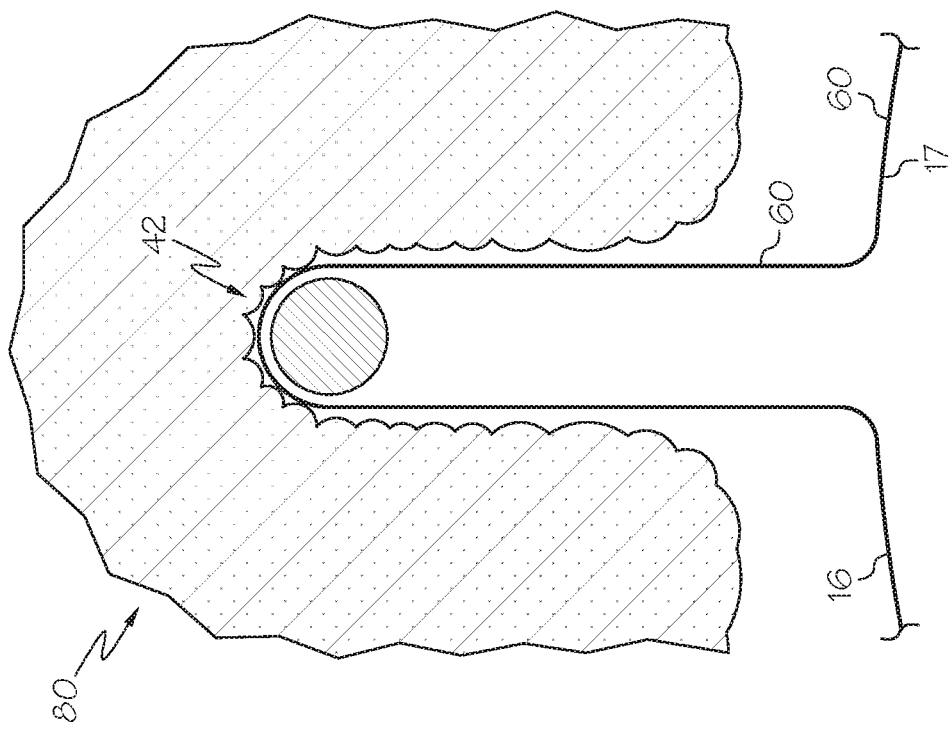
FIGS. 4-5 are cross-sectional views of the raised filament section of FIG. 3 at line A-A showing no controlled tissue ingrowth.
Figure 5:
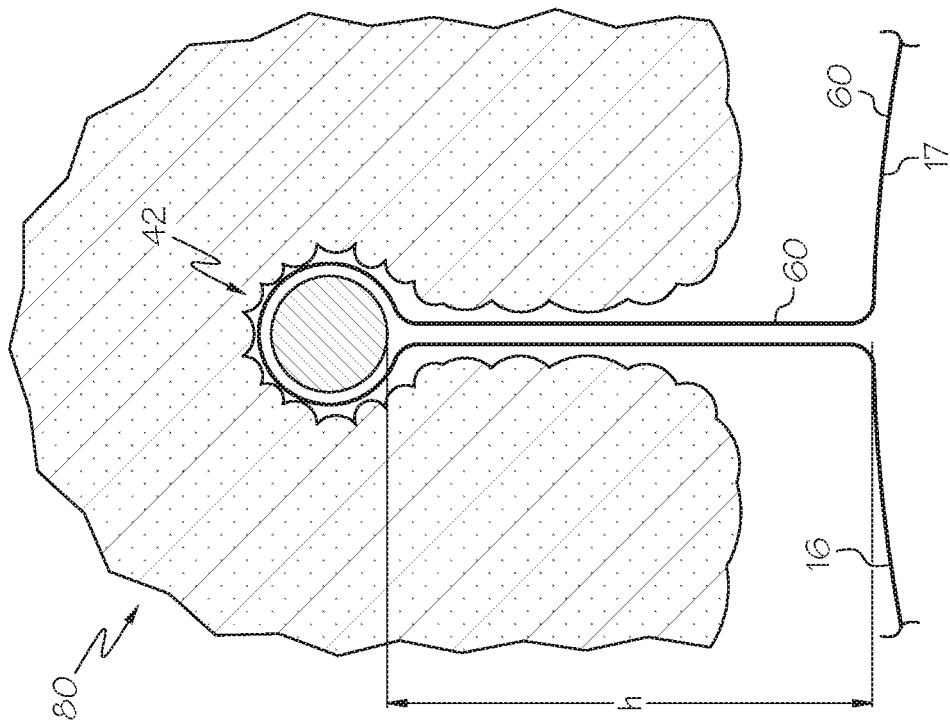
Figure 7:
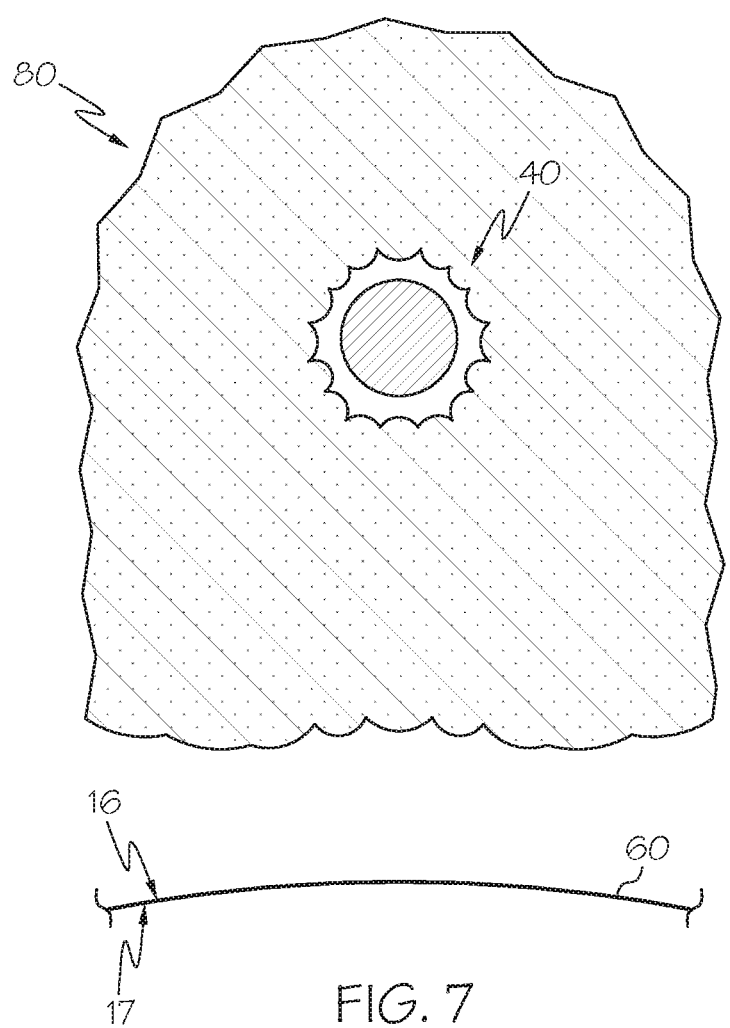
FIG. 7 is a cross-section view of the raised filament section of FIG. 6 at line A-A showing controlled tissue ingrowth.

For a protruding element 40, the pre-determined amount of tissue ingrowth also depends on whether tissue grows entirely or partially around the protruding element 40 (see e.g. FIGS. 4-5 and 7). Tissue grows entirely around a protruding element 40 with a gap 56 that is open (an "open gap"), while tissue grows partially around a protruding element 40 with a gap 56 that is closed (a "closed gap"). As used in this disclosure an "open gap" is not enclosed by, or filled with, the material forming the cover 60 (see e.g. FIG. 7), while a "closed gap" is enclosed by, or filled with, the material forming the cover 60 (see e.g. FIGS. 4-5). It is noted that the gap height h does not depend on whether the gap 56 is to be an open gap or a closed gap.

Although a prosthesis 10 with an open gap 56 may be removed after implantation, less trauma to the lumen wall 80 occurs if the prosthesis has closed gaps 56 because the cover material around the protruding element 40 provides for a passageway for removal of the protruding element 40 from the lumen wall. A prosthesis 10 may have only protruding elements 40 with open gaps 56; only protruding elements 40 with closed gaps 56; or a combination of protruding elements 40 open gaps 56 and protruding elements 40 with closed gaps 56.

A closed gap 56 may be described as being defined by a section the cover 60 extending up from the prosthesis outer surface 16, around the protruding element 40, and down to the prosthesis outer surface 16, or as a film of covering material that goes up and connects to the underside of the protruding element 40 (see e.g. FIGS. 4-5). This section of the cover 60 can be described as a gap section.

Alternatively, a closed gap 56 may be described as being formed by a layer of cover material that extends up from the prosthesis outer surface 16, around the protruding element 40, and down to the prosthesis outer surface 16. This layer of cover material forming the closed gap 56 may have a thickness less than the thickness of the cover 60.

The cover material forming a closed gap 56 may have a thickness less than the diameter of the protruding element 40 (see e.g. FIG. 4); greater than the diameter of the protruding element 40 (see e.g. FIG. 5); and combinations thereof (see e.g. FIG. 5). As used in this disclosure, a closed gap is an "enclosed closed gap" if there is a space between the material forming the cover 60 on either side of the protruding element 40, (see e.g. FIG. 4), whereas a closed gap is a "filled closed gap" if the cover material on both sides of the protruding element 40 are in contact so that there is no space therebetween (see e.g. FIG. 5).

The protruding element 40 is also constructed so that the protruding element 40 does not include any sharp turns or bends. The sharpness of a turn or bend may be described by referring to the curvature of the turn/bend. Curvature is a measure of how quickly a tangent line turns on a curve. A curve with a larger curvature bends more sharply (e.g. inside lane of a track) than another curve with a smaller curvature (e.g. outside lane of a track). Curvature is also the reciprocal of radius. Thus a small curvature implies a large radius. The turn of a protruding element 40 may have a radius of curvature of about 0.254 mm to about 0.00254 mm (0.010 inches to about 0.0001 inches). The radius of curvature is a measure of the radius of a circular arc which best approximates the curve at a particular point. An example of a "sharp" turn is a turn greater than 45° (0.785 radians) that has a radius less than 0.010 inches (0.254 mm).

C.1.a. Scaffolding Filament/Separate Filament

Figure 6:
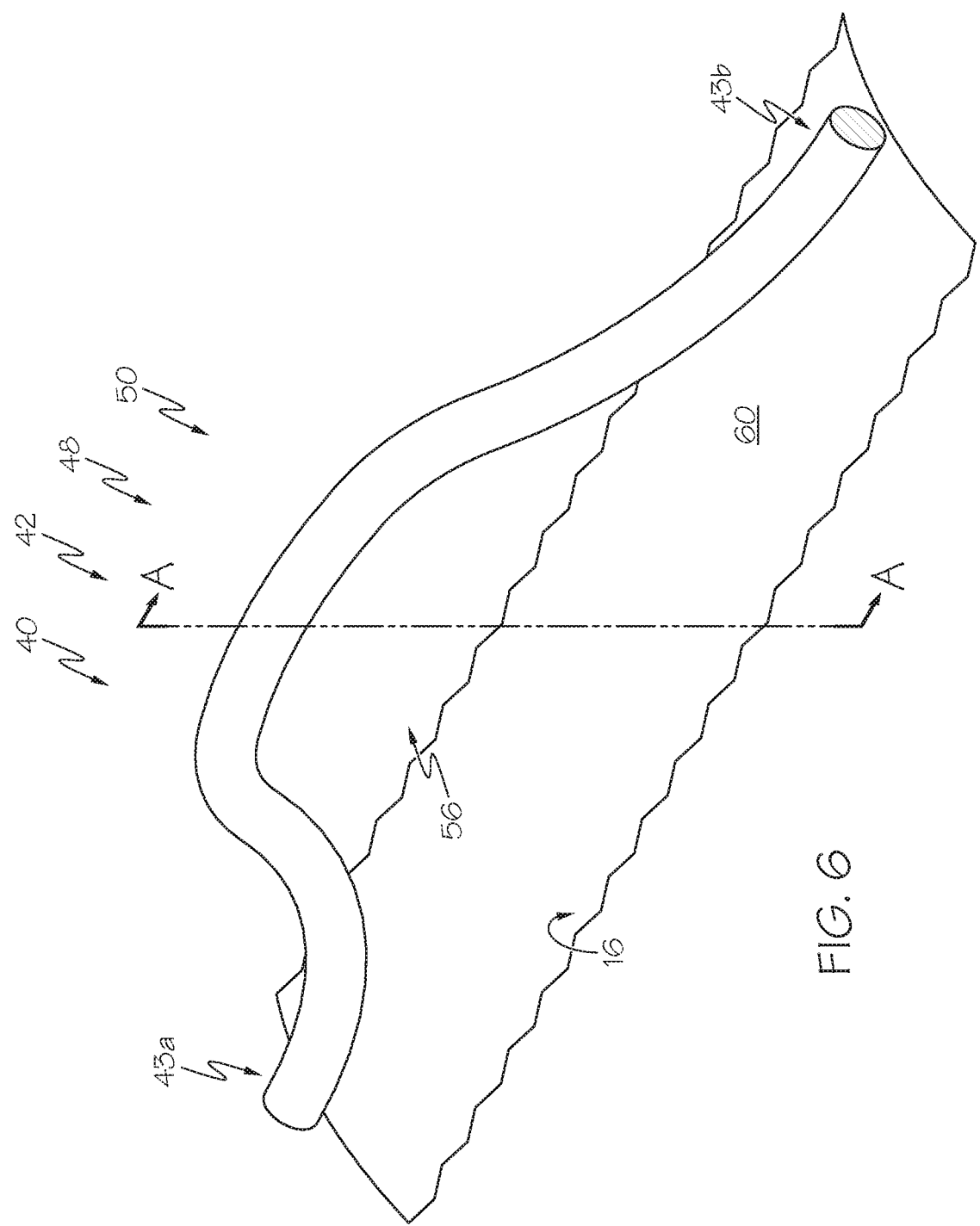
FIG. 6 is a perspective view of a raised filament section with an open gap.

As discussed above, the protruding element 40 may be a protruding scaffolding filament section 42 of a scaffolding filament 20 forming the mesh 22 (see e.g. FIG. 2), or a separate filament 48 incorporated into a mesh scaffolding 18 (see e.g. FIG. 6). In either case the protruding element 40 is formed by a single filament 20, 48. Some exemplary shapes for the protruding scaffolding filament section 42 and the separate filament 48 include rounded (see e.g. FIGS. 3 and 6); square shape (see e.g. FIG. 8A); wave shaped (see e.g. FIG. 8B); and triangular shaped (see e.g. FIG. 8C).

An individual scaffolding filament 20 of the mesh scaffolding 18 may have no protruding scaffolding filament section 42; one (1) protruding scaffolding filament section 42; or a plurality (2+) of protruding scaffolding filament sections 42. Each protruding scaffolding filament section 42 extends from a first end 43a to a second end 43b (see e.g. FIGS. 8A-C). In one aspect, each end of a protruding scaffolding filament section 42 is located at a scaffolding filament crossing 26 (see e.g. FIG. 2). The scaffolding filament crossings 26 may be positioned immediately adjacent one another (see e.g. the two scaffolding filament crossings 26 identified at the left end region of the prosthesis 10 of FIG. 1); or may be separated by at least one scaffolding filament crossing 26 (see e.g. the two scaffolding filament crossings 26 identified at the right end region of the prosthesis 10 of FIG. 1; in other words, the protruding scaffolding filament section 42 extends over, or positioned above, at least one scaffolding filament crossing 26).

Figure 8A:
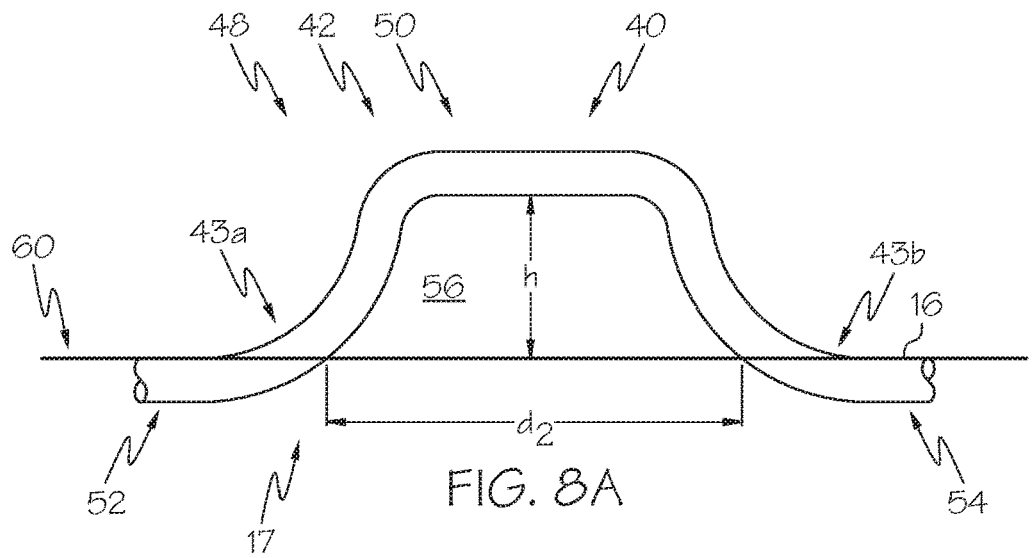
FIGS. 8A-C show exemplary shapes for a protruding element formed by a scaffolding filament or a separate filament.
Figure 8B:
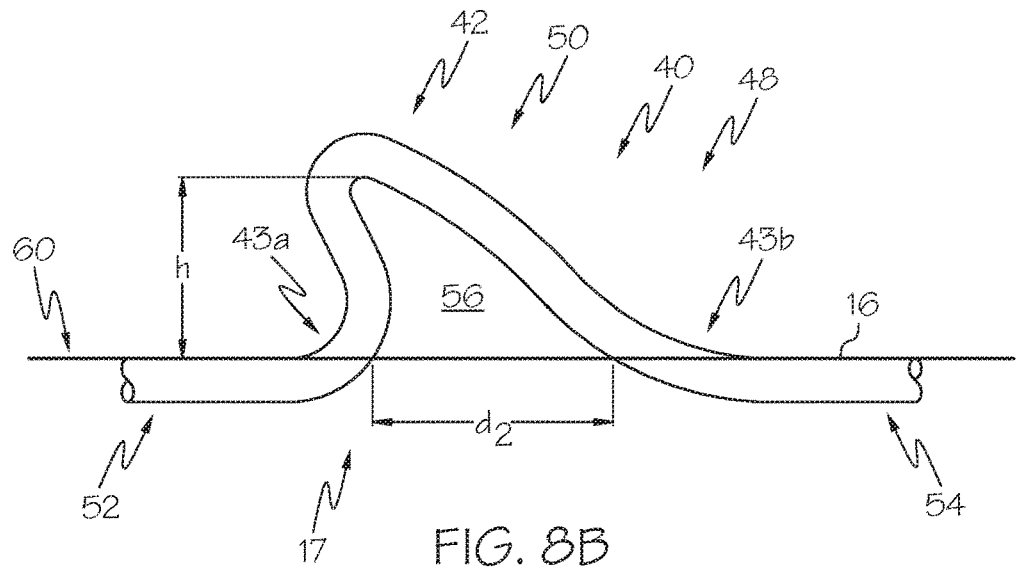
Figure 8C:
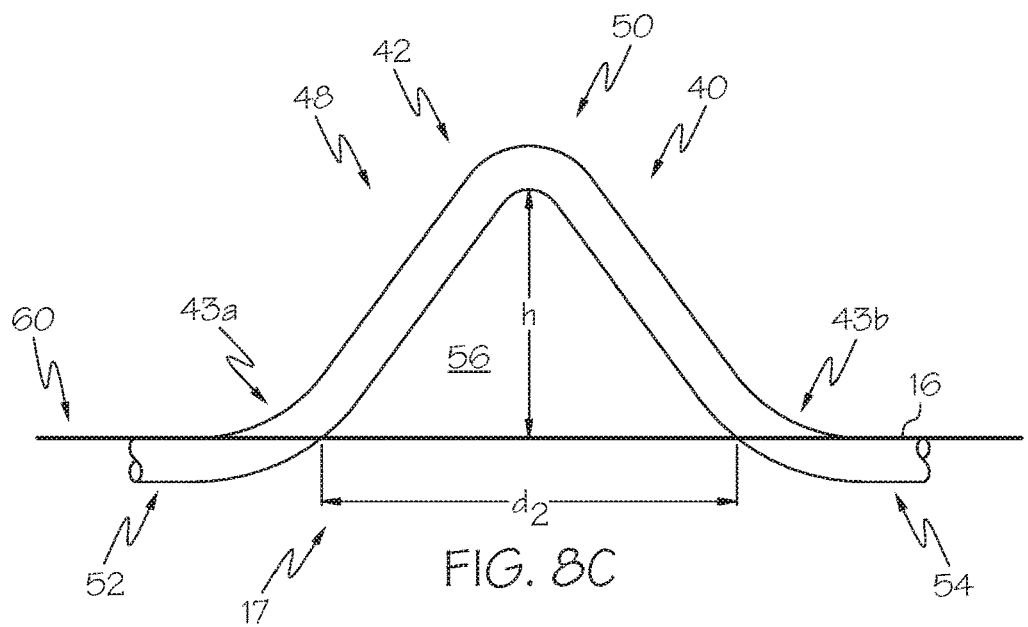

The two ends 43a, 43b of a protruding scaffolding filament section 42 are separated by a distance $d_2$ measured along the prosthesis outer surface 16 (see e.g. FIGS. 8A-C). The protruding scaffolding filament section 42 is constructed and arranged to that the distance d2 provides the cover 60 with sufficient support to withstand pressure applied by tissue ingrowth so that the cover 60 is not damaged or broken by tissue ingrowth when the prosthesis 10 is implanted. The distance d2 does not include the diameter of the scaffolding filament 20 and may be about 1.5 mm to about 7.5 mm. Where the ends 43a, 43b are located at scaffolding filament crossings 26 positioned immediately adjacent one another, the distance d2 is equal to the length of the cell/opening 24 of the braided scaffolding 18.

Each protruding scaffolding filament section 42 defines a gap 56 with a height h of about 0.5 mm to about 2 mm measured from the outer surface of the cover 60; a distance $d_2$ from the first end 43a to the second end 43b of about 1.5 mm to about 7.5 mm; and combinations thereof.

The prosthesis 10 may have at least one separate filament 48 (see e.g. FIG. 6). Each separate filament 48 has a first end region 52 forming a first filament end, a second end region 54 forming as second filament end, and a protruding section 50 with a first end 43a connected to the first end region 52 and a second end 43b connected to the second end region 54 (see e.g. FIGS. 8A-C).

The separate filament 48 may have any suitable cross-sectional shape, for example but not limited to a round cross-sectional shape or a rectangular cross-sectional shape (not shown). The separate filament 48 may have a diameter of about 0.06 mm to about 0.6 mm. The separate filament 48 has a length less than the longitudinal length of the scaffolding 18. The separate filament 48 may have a length less than the length of the scaffolding filament 20 forming the scaffolding to which the separate filament 48 is secured.

The separate filament 48 may be parallel to a scaffolding filament 20 (not shown). The end regions 52, 54 of the separate filament 48 are secured to the scaffolding 18 by any suitable manner. For example the separate filament 48 can be secured to the scaffolding 18 by interweaving the end regions 52, 54 into the scaffolding 18; by bonding the end regions 52, 54 to the scaffolding 18; by welding the end regions 52, 54 to the scaffolding 18; and/or by wrapping the end regions 52, 54 around a scaffolding filament 20. Thus, the ends of the separate filament 48 are free ends until the end regions 52, 54 are secured to the scaffolding 18. Although the separate filament 48 is secured to the scaffolding 18, the separate filament 48 is not a layer of scaffolding 18 as used herein. Thus, a prosthesis 10 with a separate filament 48 has a single layer of scaffolding 18.

Each protruding section 50 defines a gap 56 with a height h of about 0.5 mm to about 2 mm measured from the outer surface of the cover 60; a distance d2 from the first end 43a to the second end 43b of about 1.5 mm to about 7.5 mm measured along the prosthesis outer surface 16, not including the diameter of the separate filament 48; has an overall height of about 0.56 mm to about 2.6 mm; and combinations thereof.

Where a prosthesis has more than one scaffolding filament section or separate filament, the protruding scaffolding filament sections 42 or protruding sections 50 may have the same orientation, for example a right hand orientation (see e.g. FIG. 2). Further, the protruding scaffolding filament sections 42 or protruding sections 50 may be substantially aligned about the circumference of the prosthesis 10 (see e.g. FIG. 2 where the protruding scaffolding filament sections 42 have substantially the same longitudinal position but different circumferential positions).

C.1.b. Mesh Regions

Figure 9:
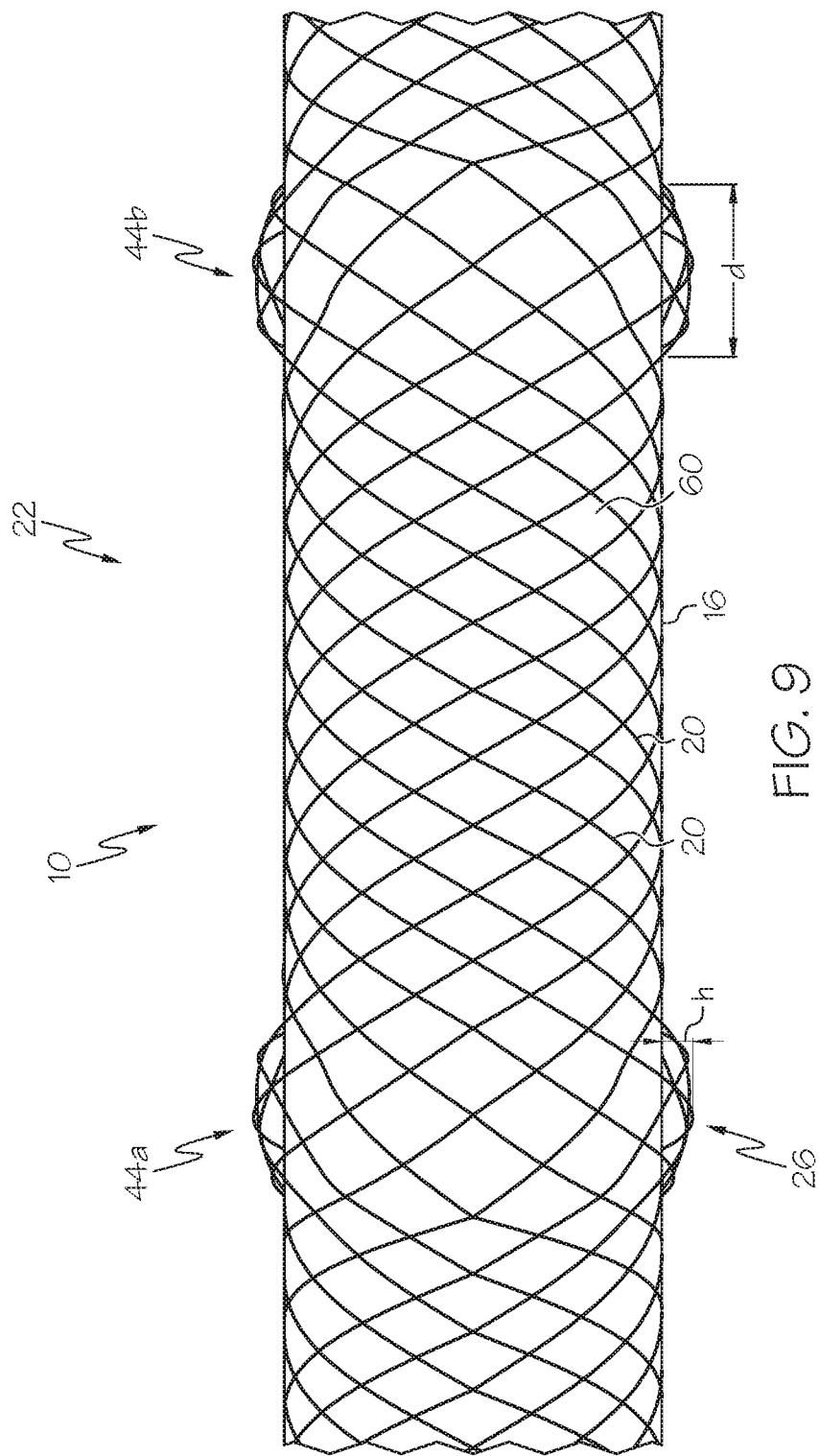
FIG. 9 is a view of a portion of an exemplary prosthesis with protruding mesh regions.

As discussed above, the protruding element 40 may be a protruding mesh region 44 (see e.g. FIG. 9). The scaffolding filament(s) 20 forming the mesh 22 and the protruding mesh region 44 may be have a uniform braid angle. In other words, the braid angle of the scaffolding filament(s) 20 in the protruding mesh region 44 is the same as the braid angle of the scaffolding filament(s) 20 in the rest of the mesh 22. An example of a suitable uniform braid angle is 100°.

The protruding mesh region 44 includes a plurality of scaffolding filament crossings 26 positioned above the prosthesis outer surface 16 which is defined by the cover 60 (see e.g. FIG. 9). The protruding mesh region 44 has a rounded shape with no sharp bends or turns (see e.g. FIG. 9). Attributes of bends/turns that are not sharp are discussed above.

The protruding mesh region 44 has a longitudinal extent/distance d measured from a first end/edge of the protruding mesh region 44 to a second end/edge of the protruding mesh region 44. The longitudinal distance d of the protruding mesh region 44 is sized so that the mesh scaffolding provides the cover 60 with sufficient support to withstand pressure applied by tissue ingrowth so that the cover 60 is not damaged or broken by tissue ingrowth when the prosthesis 10 is implanted. The longitudinal distance d may be about 2 mm to about 10 mm.

The gap height h of the protruding mesh region 44 is variable. The maximum gap height h of the protruding mesh region is about 0.5 mm to about 2 mm. The area of the gap 56 defined by a protruding mesh region 44 depends on the diameter of the prosthesis 10, the gap height h, and the longitudinal distance d of the protruding mesh region 44.

A prosthesis 10 may have one or a plurality of protruding mesh regions 44. For a prosthesis 10 with a plurality of protruding mesh regions 44, adjacent protruding mesh regions 44 are separated by a minimum longitudinal distance of about 20 mm.

C.1.c. Ring Turns

As discussed above, the prosthesis 10 may have a single layer of scaffolding 18 and a protruding element 40 (see e.g. FIGS. 10-11). The protruding element 40 may be a protruding ring turn 46 of a ring 28. Where the protruding element 40 is a protruding ring turn 46, the cover 60 may have a thickness of about 40 µm to about 400 µm.

Figure 12:
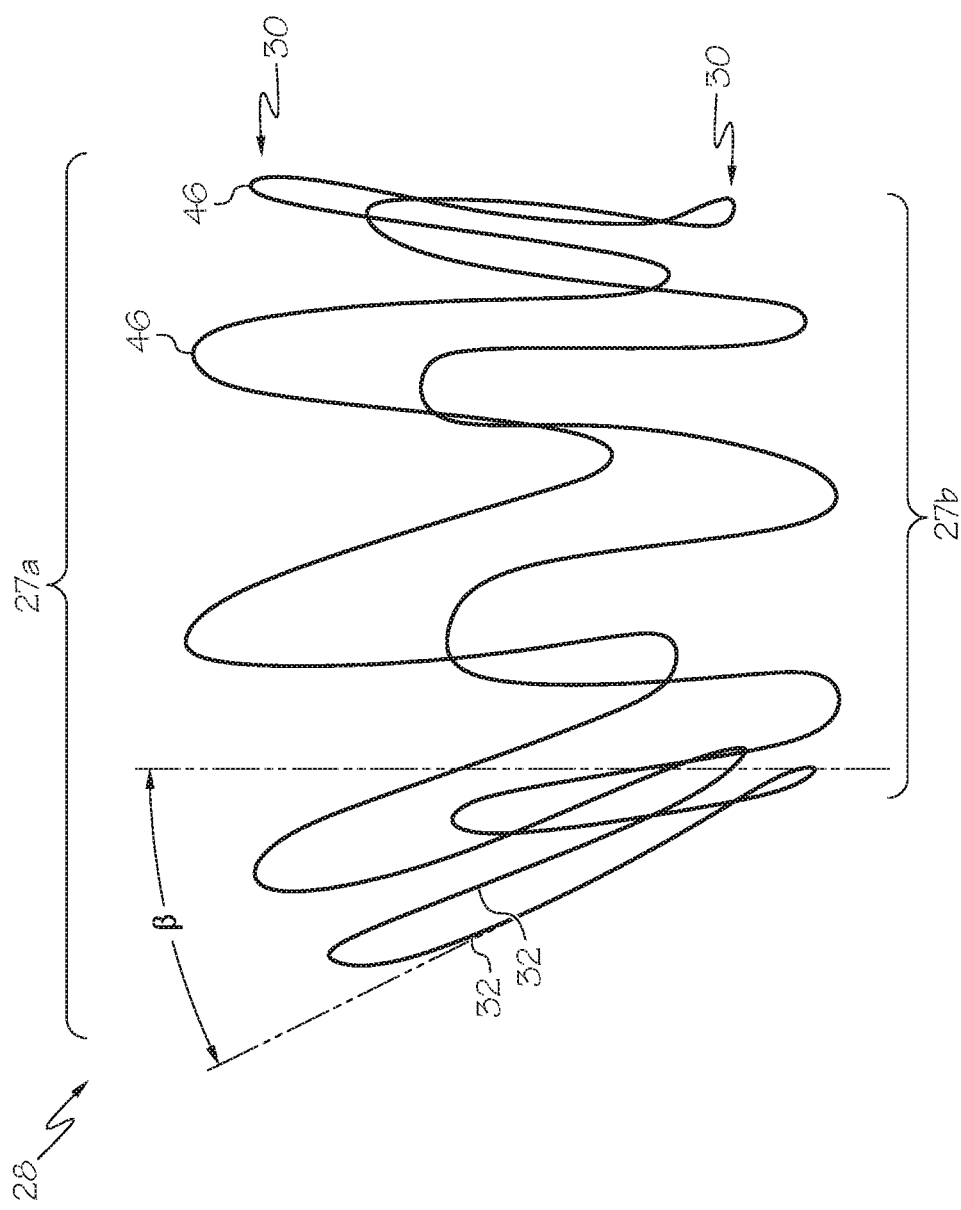
FIG. 12 is a view of an exemplary pre-formed ring.

A ring 28 with a protruding ring turn 46 may be described as having a first diameter 27a at a first ring end and a second, greater, diameter 27b at a second ring end (see e.g. FIG. 12). When a ring 28 with a larger diameter at the second ring end than the first ring end is incorporated into a prosthesis 10, the ring turns 30 at the second ring end are protruding ring turns 46 (see e.g. FIG. 12). Thus, the entire second ring end may be described as a protruding element 40.

A ring 28 with a protruding ring turn 46 may have a single, uniform slope or angle β from the first ring end to the second ring end. This type of ring 28 can be described as a truncated cone (see e.g. FIG. 12). It is noted that even when a section 32 of the scaffolding filament 20 includes a bend, the ring 28 has a single uniform slope or angle β because the bend does not affect the distance of the protruding ring turn from the outer surface of the cover 60. Alternatively a ring 28 with a protruding ring turn 46 may have a cylindrical section and a truncated cone section, where the cylindrical section forms one end of the ring 28 and has a uniform diameter, and the truncated cone section forms the other end of the ring 28 and has a single, uniform slope or angle from the cylindrical section to the end of the ring 28. A ring 28 with either of these two configurations has protruding ring turns 46 that extend outwardly at a single uniform slope or angle β.

As discussed above, the ring 28 has a longitudinal length. About 25-75% of the longitudinal length of the ring 28, as measured from the first and second ring ends, may be positioned above the outer surface of the cover 60. Thus for a ring 28 in the shape of a truncated cone, a protruding ring turn 46 may include a portion of each of the two sections 32 connected the protruding ring turn 46 (see e.g. FIG. 13A). For a ring 28 with a cylindrical section and a truncated cone section, the truncated cone section is constructed and arranged to be positioned above the outer surface of the cover 60. Thus, the truncated cone section may have a length of about 25% to about 75% of the longitudinal length of the ring 28.

Figure 13A:
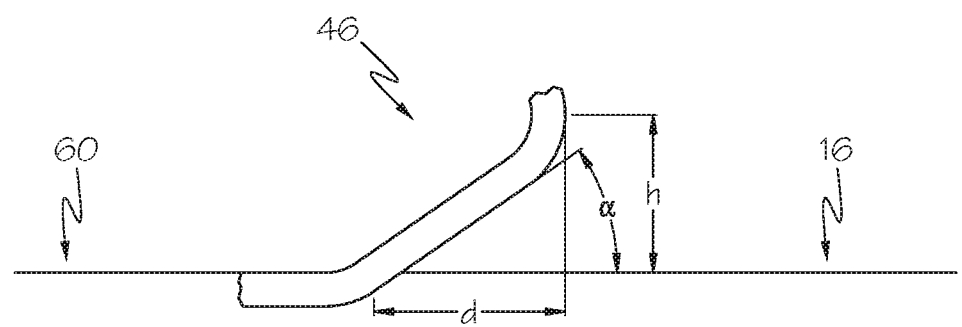
FIGS. 13A-B show schematic views of a protruding ring turn.
Figure 13B:
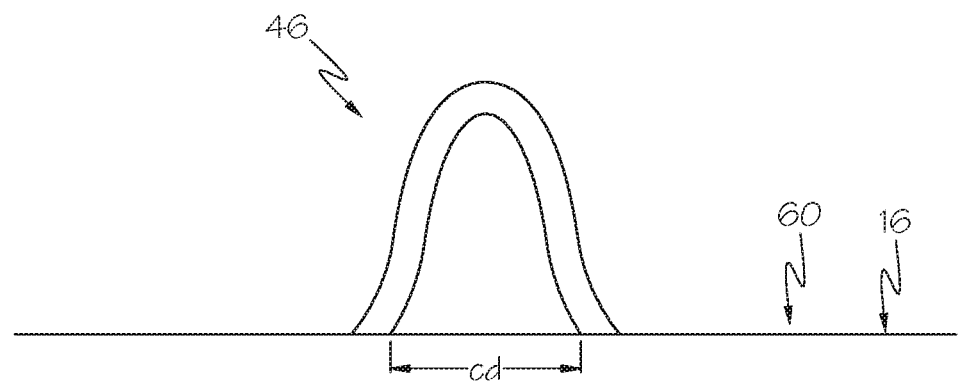
Figure 14:
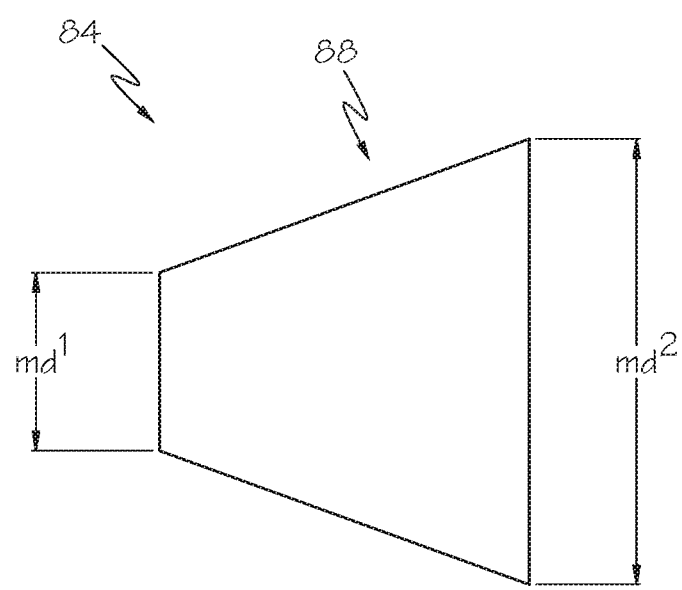
FIG. 14 is a schematic view of a tapered mandrel section for forming a ring.

The protruding ring turn 46 has a gap height h of about 0.25 mm to about 4 mm, preferably about 0.25 mm to about 2 mm (see e.g. FIGS. 13A-B). For a given uniform slope β, the gap height h correlates either to the percentage of the longitudinal length of the ring 28 or to the percentage of the truncated cone section that is positioned above the outer surface of the cover 60. For example, for a given uniform slope β, the greater the percentage of the ring or truncated cone section that is positioned above the outer surface of the cover, the greater the gap height h. In other words, the gap height h at 25% is greater than the gap height h at 75%. For a given gap height h, the uniform slope β correlates to the percentage of the longitudinal length of the ring 28 or the percentage of the truncated cone section that is positioned above the outer surface of the cover 60. For example, for a given gap height h, the greater the percentage of the ring or truncated cone section that is positioned above the outer surface of the cover, the greater the uniform slope β. In other words, a greater uniform slope β is needed to obtain a given gap height when 75% is positioned above the outer surface of the cover than when 25% is positioned above the outer surface of the cover.

A prosthesis 10 has at least one ring 28 with a protruding ring turn 46. A prosthesis 10 may comprise only rings 28 having at least one protruding ring turn 46 (see e.g. FIG. 10); or a combination of rings 28a having at least one protruding ring turn 46, and rings 28b having no protruding ring turns (see e.g. FIG. 11). The protruding ring turns 46 of a prosthesis 10 may be oriented toward the same prosthesis end 12, 14, or may be oriented towards both prosthesis ends 12, 14 (see e.g. FIGS. 10-11). An individual ring 28 may have protruding ring turns 46 facing toward only one prosthesis end 12, 14, or protruding ring turns 46 facing both prosthesis ends 12, 14.

C.2. Inwardly Extending Controlled Ingrowth Feature/Dimple

A controlled ingrowth feature 40 that extends inwardly can be described as an inwardly extending controlled ingrowth feature or as a dimple (hereinafter referred to as a "dimple"). In other words, a dimple 40 is positioned a smaller distance from, or is closer to, the longitudinal axis of the prosthesis than the prosthesis outer surface 16 (see e.g. FIGS. 15A-21C). As used in this disclosure, a "dimple" extends inwardly from a prosthesis outer surface 16 of an implanted prosthesis and has an edge positioned at the prosthesis outer surface 16. For a prosthesis 10 comprising a dimple 40, the prosthesis outer surface 16 is defined by the cover 60.

A dimple 40 may be entirely formed by a portion of the cover 60 extending over the outer surface of the scaffolding 18 (see e.g. FIGS. 15A-18 and 20); may be formed by a portion of the cover 60 and a portion of the scaffolding 18 (see e.g. FIG. 19); may be formed by a dimple patch 68 (see e.g. FIGS. 21A-C); and combinations thereof.

A dimple 40 has a longitudinal extent (distance d) measured along the prosthesis outer surface 16 of about 1 mm to about 10 mm; a circumferential extent measured along the prosthesis outer surface 16 of about 1 mm to about 10 mm; an area of about 1 mm$^2$ to 100 mm$^2$, preferably about 5 mm$^2$ to about 50 mm$^2$, most preferably 25 mm$^2$; and combinations thereof. Where the longitudinal or circumferential extent is variable, the longitudinal/circumferential extent refers to the maximum extent.

As discussed above, the pre-determined amount of tissue ingrowth depends in part on the amount of the prosthesis outer surface 16 that is formed by the dimple(s) 40. The dimple(s) cover a maximum of about 30% of the scaffolding outer surface. The dimple(s) 40 may cover about 1% to about 30% of the scaffolding outer surface, preferably about 5% to about 20% of the scaffolding outer surface, and most preferably 10% of the scaffolding outer surface.

When the prosthesis 10 expands to an implanted diameter, the dimple 40 defines a gap 56 for tissue ingrowth (see e.g. FIGS. 16B and 17-19). The gap 56 of a dimple 40 may also be described as a dimple gap or dimple recess. It is noted that the dimple 40 may or may not extend inward into the prosthesis lumen at other times (e.g. during delivery). A dimple 40 may define one (1) dimple gap 56 (see e.g. FIGS. 17-19); or a plurality of dimple gaps 56 (see e.g. FIG. 16B). The dimple gap 56 is constructed and arranged so that the dimple 40 does not exert suction on the lumen wall when the prosthesis 10 is implanted. A dimple gap 56 may extend inward through a single scaffolding opening 24 (see e.g. FIG. 16B) or span several scaffolding openings (see e.g. FIGS. 18 and 20-21C). The scaffolding opening 24 into which the dimple 40 extends may have a size equal to the other scaffolding openings 24 (see e.g. FIG. 16B), or greater than the other scaffolding openings 24 (see e.g. FIG. 17).

The dimple gap 56 has a maximum gap height h measured from the outer surface of the cover 60 to the bottom of the dimple gap 56 (see e.g. FIGS. 16B-19). The maximum gap height h is about 0.5 mm to about 3 mm, preferably about 1 mm to about 2 mm, and most preferably about 1.5 mm. The overall size of the dimple gap 56 depend at least in part on the size of the scaffolding openings 24; the gap height h; and combinations thereof (see e.g. FIGS. 16A-16C and 21A-21C).

A prosthesis 10 with a dimple 40 may have a single layer of scaffolding 18 (see e.g. FIGS. 16A-19 and 21A-22) or two layers of scaffolding 18 (see e.g. FIG. 20). The prosthesis 10 may have a single (1) dimple 40 or a plurality of dimples 40. The dimple(s) 40 may be arranged in a circumferential ring (see e.g. FIGS. 15A-C and 24C); helically (see e.g. FIG. 24A); an island surrounded by a non-dimple portion of the prosthesis (see e.g. FIGS. 15A-C and 24A-C); and combinations thereof. Where the dimple 40 forms a circumferential ring, the ring may extend around the entire circumference of the prosthesis 10 or only a portion of the circumference of the prosthesis 10. For each of these arrangements the dimple 40 covers only a portion of the outer surface area of the prosthesis 10 and only a portion of the inner surface area of the prosthesis 10.

C.2.a. Inwardly Extending Controlled Ingrowth Feature/Dimple Entirely Formed by Cover As discussed above, a dimple 40 may be entirely formed by the cover 60 (see e.g. FIGS. 15A-18 and 20). Thus the cover 60 has at least one dimple cover section 64 forming a dimple 40. Each dimple cover section 64 is entirely surrounded by a non-dimple cover section 66 of the cover 60 (see e.g. FIG. 15A). As used herein a "non-dimple cover section" is a section of the cover 60 that has a size equal to the size of the scaffolding covered thereby, and a "dimple cover section" is a section of the cover 60 that has a size greater than the size of the scaffolding covered thereby.

A cover 60 with a dimple cover section 64 and a non-dimple cover section 66 may have a uniform thickness. In other words, the thickness of the dimple cover section 64 is equal to the thickness of the non-dimple cover section 66.

Scaffolding 18 may extend over a gap 56 formed by the dimple 40 (see e.g. FIG. 20). The scaffolding extending over the gap 56 may be a portion of the scaffolding 18 forming the prosthesis (see e.g. FIG. 18), or a scaffolding patch 18b attached to the prosthesis outer surface 16 (see e.g. FIG. 20). Where the scaffolding extending over the gap is a portion of the scaffolding 18, the prosthesis 10 has a single layer of scaffolding 18.

Where the scaffolding extending over the gap 56 is a scaffolding patch 18b, the prosthesis 10 may be described as having two layers of scaffolding. However, only one of the two layers of scaffolding extends from the first prosthesis end 12 to the second prosthesis end 14. The other layer of scaffolding 18, the scaffolding patch 18b, has a patch longitudinal extent pd and a patch circumferential extent that is sufficiently large to cover the gap 56 but extends over only a portion of the scaffolding 18. In other words, the area of the scaffolding patch 18b is less than the outer surface area of the prosthesis 10. A scaffolding patch may be attached to the prosthesis outer surface 16 by any suitable means.

C.2.b. Inwardly Extending Controlled Ingrowth Feature/Dimple Formed by Cover and Scaffolding As discussed above, a dimple 40 may be formed by a portion of the cover 60 and a portion of the scaffolding 18 (see e.g. FIG. 19). Hereinafter, this type of dimple is referred to as a reinforced dimple 40. Because the scaffolding 18 forms a part of the reinforced dimple 40, the prosthesis 10 has a variable diameter.

The scaffolding 18 of a reinforced dimple 40 may be positioned between the outer and inner surface of the reinforced dimple, or may form a part of the inner surface of the reinforced dimple.

C.2.c. Inwardly Extending Controlled Ingrowth Feature/Dimple Patch

Figure 21A:
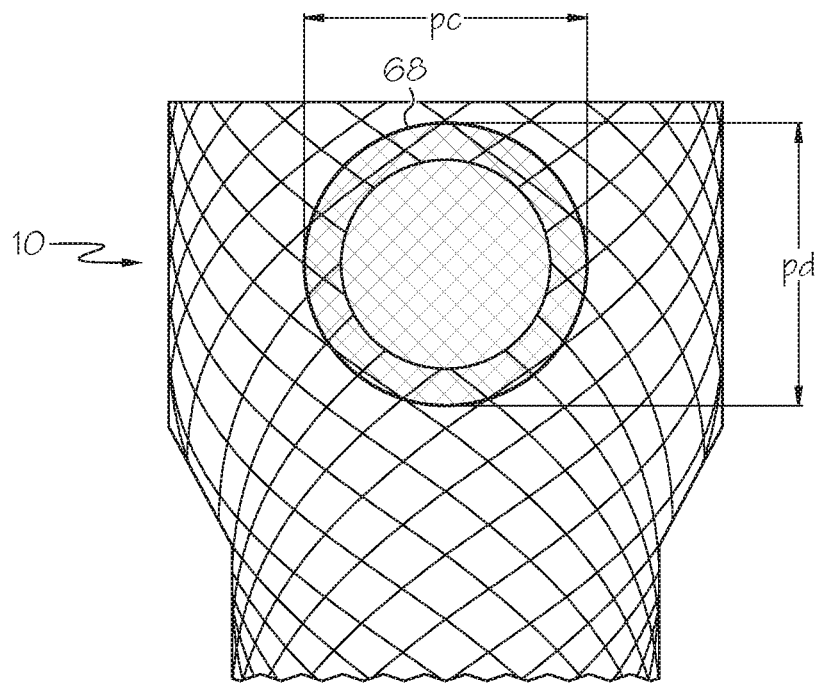
FIGS. 21A-C are views of an exemplary method of forming a dimple.
Figure 21B:
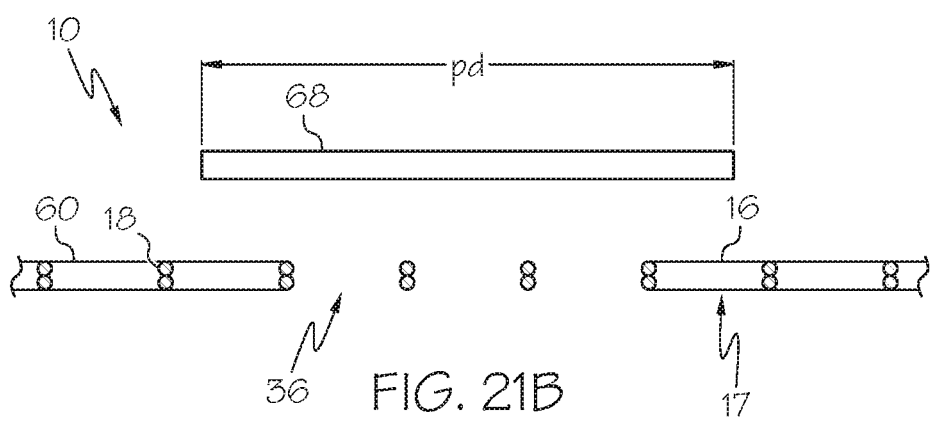
Figure 21C:
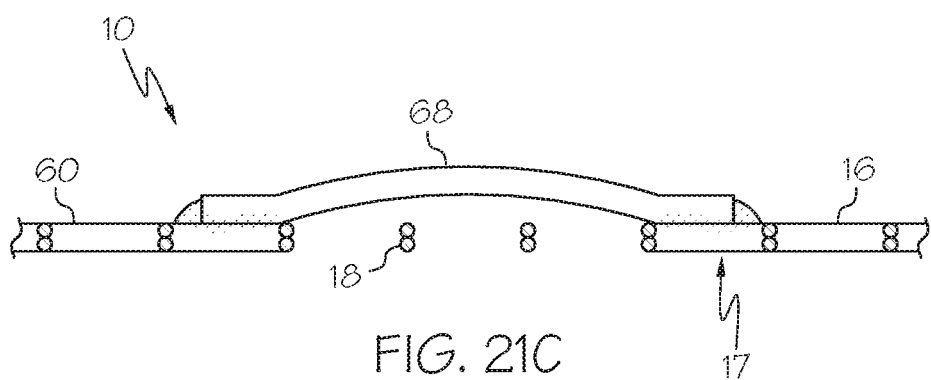

As discussed above, a dimple 40 may be formed by a dimple patch 68 (see e.g. FIGS. 21A-C). The dimple patch 68 may cover an area 36 with no cover (see e.g. FIG. 21B). The size of the area 36 may be greater than the size of the scaffolding openings 24. The size of the dimple patch 68 is greater than the size of the area 36 but less than the size of the cover 60. In other words, the surface area covered by the dimple patch 68 is less than outer surface area of the cover 60. The size of the dimple patch 68 is also sufficiently large to form a dimple 40 when the prosthesis is implanted.

The area 36 may include scaffolding 18 (portion of scaffolding with no cover, see e.g. FIGS. 21B-C); or no scaffolding. Any suitable means can be used to form an area 36 with no scaffolding. For example, a region of the scaffolding 18 may be removed leaving an opening with a greater size than the scaffolding openings 24; or formation of the area 36 may be a part of forming the scaffolding, e.g. forming the scaffolding includes forming a scaffolding opening 24 that is larger than other scaffolding openings 24.

Figure 24C:
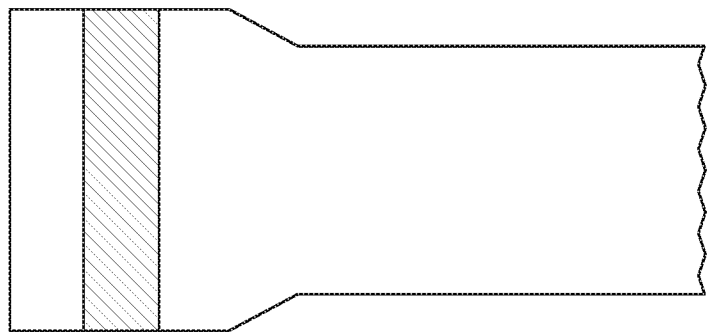
FIGS. 24A-C are exemplary configurations of a controlled ingrowth feature.
Figure 24B:
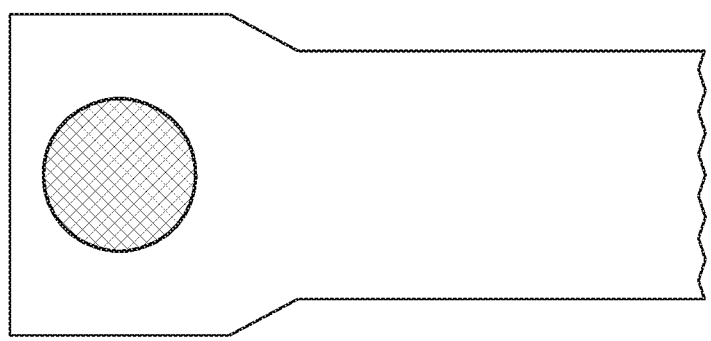
Figure 24A:
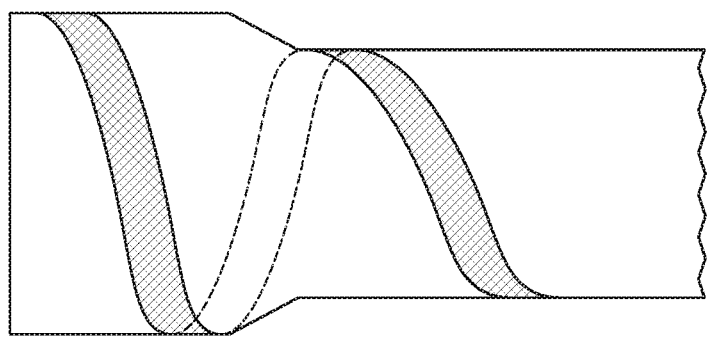

As can be seen in FIGS. 24A-C, the dimple patch 68 is attached to the prosthesis outer surface 16. The dimple patch 68 may be attached to the prosthesis outer surface 16 by any suitable means.

A scaffolding patch may be combined with a dimple patch 68. The scaffolding patch has a size equal to or less than the size of the dimple patch. The scaffolding patch may be positioned over the dimple patch 68. This configuration may look similar to that shown in FIG. 20 except that the wall of the prosthesis will have three layers, an inner layer of scaffolding; a middle layer formed by the dimple patch 68 extending over an area 36; and an outer layer formed by the scaffolding patch. This type of dimple patch can be described as a reinforced dimple patch. Alternatively, the scaffolding patch may be positioned between the inner and outer surfaces of the dimple patch.

D. Optional Prosthesis Features

A prosthesis 10 as described above may include one or more areas, bands, coatings, members, etc. that is (are) detectable by imaging modalities such as X-Ray, MM, ultrasound, etc. In one aspect at least a portion of the prosthesis 10 is at least partially radiopaque.

A prosthesis 10 as described above may be configured to include one or more mechanisms for the delivery of a therapeutic agent. As used in this disclosure, a "therapeutic agent" is a drug or other pharmaceutical product used to treat, preventing, or alleviating the symptoms of disease, and is not a cover 60 as disclosed herein. Therapeutic agents include non-genetic agents, genetic agents, cellular material, etc. Often the agent will be in the form of a coating or other layer (or layers) of material placed on a surface region of the prosthesis, which is adapted to be released at the site of the prosthesis' implantation or areas adjacent thereto. In some embodiments, the controlled ingrowth feature 40 has a therapeutic agent deposited thereon.

PROSTHESIS EXAMPLES

Exemplifications of a prosthesis 10 as described above are provided by the following non-limiting examples.

Example 1

FIG. 2 shows an example of a prosthesis 10 with at least protruding element 40. Specifically, the prosthesis 10 has a single layer of scaffolding 18 in the form of a mesh 22 with a protruding scaffolding filament section 42; and a cover 60.

The prosthesis has a longitudinal length of 102 mm. The end regions of the prosthesis 10 have a greater diameter than the middle region, with the end regions having a diameter of 30 mm, and the middle region having a diameter of 23 mm.

The scaffolding 18 is formed from 24 scaffolding filaments 20 each having a diameter of 0.009 mm, and comprises Nitinol. The scaffolding filaments 20 are braided at a uniform braiding angle.

The cover 60 is non-porous.

In this example, each scaffolding filament 20 with a right hand orientation has a protruding scaffolding filament section 42 extending between two scaffolding filament crossings 26 immediately adjacent one another, and each protruding scaffolding filament section 42 has a closed gap 56 and a rounded shape with no sharp bends. Further, the protruding scaffolding filament sections 42 are substantially aligned about the circumference of the prosthesis 10. As can be seen a right hand orientation is non-parallel to the longitudinal axis of the prosthesis.

Example 2

FIG. 9 shows another example of a prosthesis 10 with at least one controlled tissue ingrowth feature 40. Specifically, the prosthesis 10 has a single layer of scaffolding 18 in the form of a mesh 22 with two protruding mesh regions 44a, 44b; and a cover 60.

The prosthesis 10 has a diameter of 23 mm and a longitudinal length of 150 mm. The prosthesis 10 may have a uniform diameter except for the protruding mesh regions 44. However, the ends of the prosthesis, not shown in FIG. 9, may have a greater diameter than the uniform diameter section shown in FIG. 9. The scaffolding 18 is formed from 24 scaffolding filaments 20 each having a diameter of 0.008 mm and comprises Nitinol.

The cover 60 is non-porous and has a thickness of 40 µm.

Each protruding mesh region 44a, 44b forms a circumferential ring that extends around the entire circumference of the prosthesis; has a gap height h of 1 mm; and a longitudinal distance d of 10 mm. A longitudinal distance of 40 mm separates the two protruding mesh regions 44a, 44b and each protruding mesh region 44a, 44b is 45 mm from the closest prosthesis end 12, 14.

Example 3

FIG. 10 shows another example of a prosthesis 10 with at least one protruding element 40. The prosthesis 10 shown in FIG. 10 is constructed and arranged for implantation in the esophagus.

The prosthesis has a longitudinal length, and prosthesis end regions with a greater diameter than the prosthesis middle region.

The prosthesis 10 has a single layer of scaffolding 18 consisting of rings 28 with protruding ring turns 46; and a cover 60.

The prosthesis 10 has rings 28 with protruding ring turns 46. Half of the rings 28 have protruding ring turns 46 oriented towards the second prosthesis end 14, and half of the rings 28 have protruding ring turns 46 oriented towards the first prosthesis end 12. Adjacent rings 28 are separated by a uniform longitudinal distance 34.

The cover 60 is non-porous and comprises silicone.

Example 4

FIG. 11 shows another example of a prosthesis 10 with at least one protruding element 40. The prosthesis 10 shown in FIG. 11 is constructed and arranged for implantation in the stomach.

The prosthesis 10 has a single layer of scaffolding 18 formed of rings 28 where at least some of the rings 28 have protruding ring turns 46; and a cover 60.

The prosthesis 10 has a longitudinal length and a variable diameter with a minimum diameter of 15 mm, and a maximum diameter of 40 mm. Adjacent rings 28 are separated by a variable longitudinal distance (e.g. distances 34a, 34b). The rings 28 include rings 28a with a protruding ring turn 46, and rings 28b with no protruding ring turns 46. The rings 28a with protruding ring turns 46 are arranged in two groups. Within each group the protruding ring turns 46 of an individual ring 28a are oriented towards one prosthesis end and the adjacent ring 28a is oriented toward to other prosthesis end 12, 14. In other words, within a group of rings 28a, the orientation of the protruding ring turns 46 alternates.

Each ring 28 is formed by a scaffolding filament 20 comprising Nitinol.

The cover 60 is non-porous.

Example 5

Figure 15A:
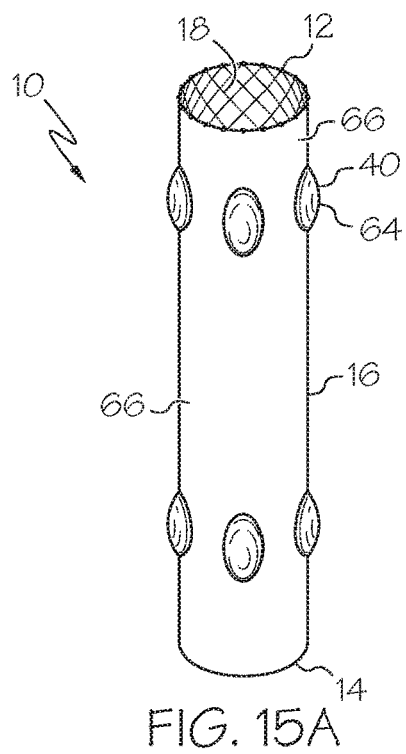
FIGS. 15A-C are schematic views of exemplary prostheses with dimples
Figure 15B:
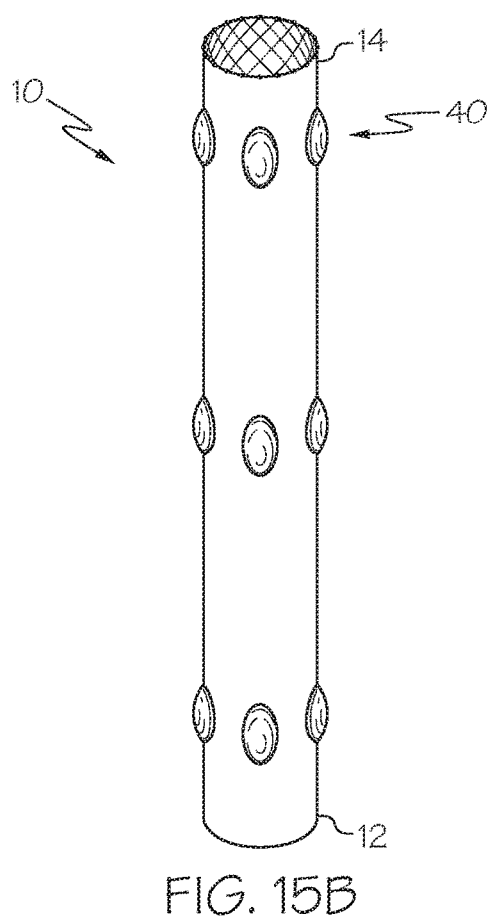
Figure 15C:
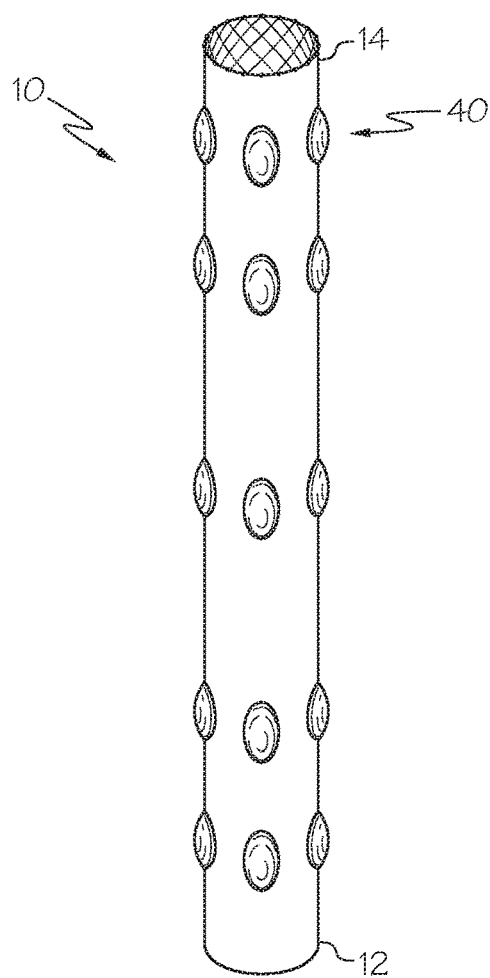

FIGS. 15A-C show examples of a prosthesis with a dimple 40. Specifically, the prosthesis 10 has a single layer of scaffolding 18 in the form of a mesh 22, and a cover 60 defining at least one dimple 40.

The prosthesis has a longitudinal length of 100 mm and a diameter of 24 mm.

The cover 60 has a thickness of 0.05-0.15 mm and forms the prosthesis outer surface 16. The cover 60 has a plurality of dimple sections 64 each forming a dimple 40; and a non-dimple section 66.

Each dimple 40 is positioned at least 15 mm from the closest prosthesis end 12, 14; has a maximum longitudinal extent of 12.7 mm; a maximum circumferential extent of 6 mm; and define a gap of 2 mm. The dimples 40 are aligned circumferentially and longitudinally. For the prosthesis 10 shown in FIG. 15A, longitudinally adjacent dimples 40 are positioned 44.6 mm apart.

Methods of Manufacture

In general, forming a prosthesis as described above includes: forming the scaffolding; forming a controlled ingrowth feature; and applying a cover to the scaffolding. Forming the controlled ingrowth feature may be a part of forming the scaffolding; a part of forming the cover; or a separate step. Thus, when the prosthesis is formed, the prosthesis has a scaffolding; a cover; and a controlled ingrowth feature. Manufacturing or formation of the prosthesis is completed before the prosthesis is engaged to a delivery device.

Method 1

An exemplary method of forming a prosthesis 10 with a protruding element 40 formed by a separate filament 48 includes one or more of the following: forming the scaffolding 18 by interweaving a scaffolding filament 20 into a mesh; securing a separate filament 48 to the scaffolding 18; forming a protruding element 40 from the separate filament 48, the protruding element 40 being a section 50 of the separate filament 48; applying a cover 60 to the scaffolding 18; wherein securing the separate filament 48 to the scaffolding 18 further comprises securing each end region 52, 54 of the separate filament 48 to the scaffolding 18; wherein the end regions 52,54 may be secured by interweaving into the scaffolding 18; by bonding to the scaffolding 18; by welding to the scaffolding 18; by wrapping the end regions 52,54 around a scaffolding filament 20; and combinations thereof; wherein the scaffolding 18 is formed before the separate filament 48 is secured to the scaffolding 18; wherein the scaffolding filament 20 is interwoven on a mandrel; wherein the mandrel has a constant diameter; wherein the mandrel has end mandrel regions with a greater diameter than a middle mandrel region; and combinations thereof.

Method 2

An exemplary method of forming a prosthesis 10 with a protruding element 40 formed by a scaffolding filament 20 includes one or more of the following: forming the scaffolding 18 by interweaving a scaffolding filament 20 into a mesh; forming a protruding element 40 from a section 42 of the scaffolding filament 20; applying a cover 60 to the scaffolding 18; wherein the scaffolding filament is interwoven on a mandrel; wherein the mandrel has a constant diameter; wherein the mandrel has end mandrel regions with a greater diameter than a middle mandrel region; and combinations thereof.

A prosthesis formed by this method can have only protruding elements 40 with open gaps; only protruding elements with closed gaps; or a combination of protruding elements 40 with open gaps and protruding elements 40 with closed gaps.

Method 3

An exemplary method of forming a prosthesis 10 with a protruding mesh region 44 includes one or more of the following: forming the scaffolding 18 by interweaving a scaffolding filament 20 into a mesh; forming a protruding mesh region 44; and applying a cover 60 to the scaffolding 18, wherein the protruding element 40 is positioned above the cover 60; removing the covered prosthesis from the mandrel; interweaving the scaffolding filament 20 on a mandrel; wherein the mandrel has a constant diameter; wherein the mandrel has end mandrel regions with a greater diameter than a middle mandrel region; and combinations thereof.

Method 4

In one aspect, a method of forming a ring 28 with protruding ring turns 46 includes one or more of the following: forming a ring with a plurality of interconnected ring turns 30; wherein forming the ring with the plurality of interconnected ring turns 30 comprises winding a single (1) scaffolding filament 20 around a mandrel and securing the ends of the scaffolding filament 20; wherein securing the ends of the scaffolding filament 20 comprises welding, joining by clips, applying adhesive, and combinations thereof; wherein the mandrel 84 includes a tapered section with a first mandrel diameter md1 and a second mandrel diameter md2 greater than the first diameter, and a slope from the first mandrel diameter to the second mandrel diameter (see e.g. FIG. 14); wherein the slope from the first mandrel diameter to the second mandrel diameter provides for the uniform angle β of the ring 28 from the first diameter 27*a* to the second diameter 27*b*; wherein the mandrel further includes a cylindrical section with a second uniform mandrel diameter; wherein the slope of the tapered section of the mandrel from the cylindrical section to the second mandrel diameter provides for the uniform angle β of the ring from the cylindrical section of the ring to the second diameter of the ring; wherein the ring turns 30 formed at the second mandrel diameter will be protruding ring turns 46 when incorporated into a prosthesis 10; wherein the mandrel includes protrusions extending outwardly from the outer surface of the mandrel 84; wherein the single scaffolding filament 20 further forms a plurality of sections 32, each section 32 extending between two ring turns 30; wherein forming the ring with the plurality of interconnected ring turns 30 comprises injection molding a filament material into a mold with a desired shape for the ring; wherein the filament material is polymeric; wherein the prosthesis 10 has a single layer of scaffolding 18; and combinations thereof.

Method 5

An exemplary method of forming a prosthesis 10 includes one or more of the following: mounting the rings 28 onto a mandrel, each ring 28 comprising a plurality of interconnected ring turns 30, at least one of the rings 28 has a first end with a smaller diameter than a second end; applying a cover 60, the cover 60 interconnecting the rings 28; wherein the mandrel has a constant diameter; removing the prosthesis 10 from the mandrel; wherein the mandrel has end regions with a greater diameter than a mandrel middle region; wherein all of the rings have a first end with a smaller diameter than a second end; wherein dip-coating is used for applying the cover; wherein spray-coating is used for applying the cover; wherein the cover comprises silicone; and combinations thereof.

Method 6

An exemplary method of forming a cover 60 with a dimple cover section 64 comprises one or more of the following: forming a cover template 94 with a dimple; mounting a film in dimple forming device 90; forming a dimple 40 in the film; wherein the dimple forming device comprises a plate 92 with a surface defining an indentation; wherein the pattern of the indentation corresponds to a predetermined pattern for the cover 60; wherein forming a dimple in the film comprises pressing the film into the indentation; wherein the film comprises polytetrafluoroethylene; and combinations thereof.

Figure 23:
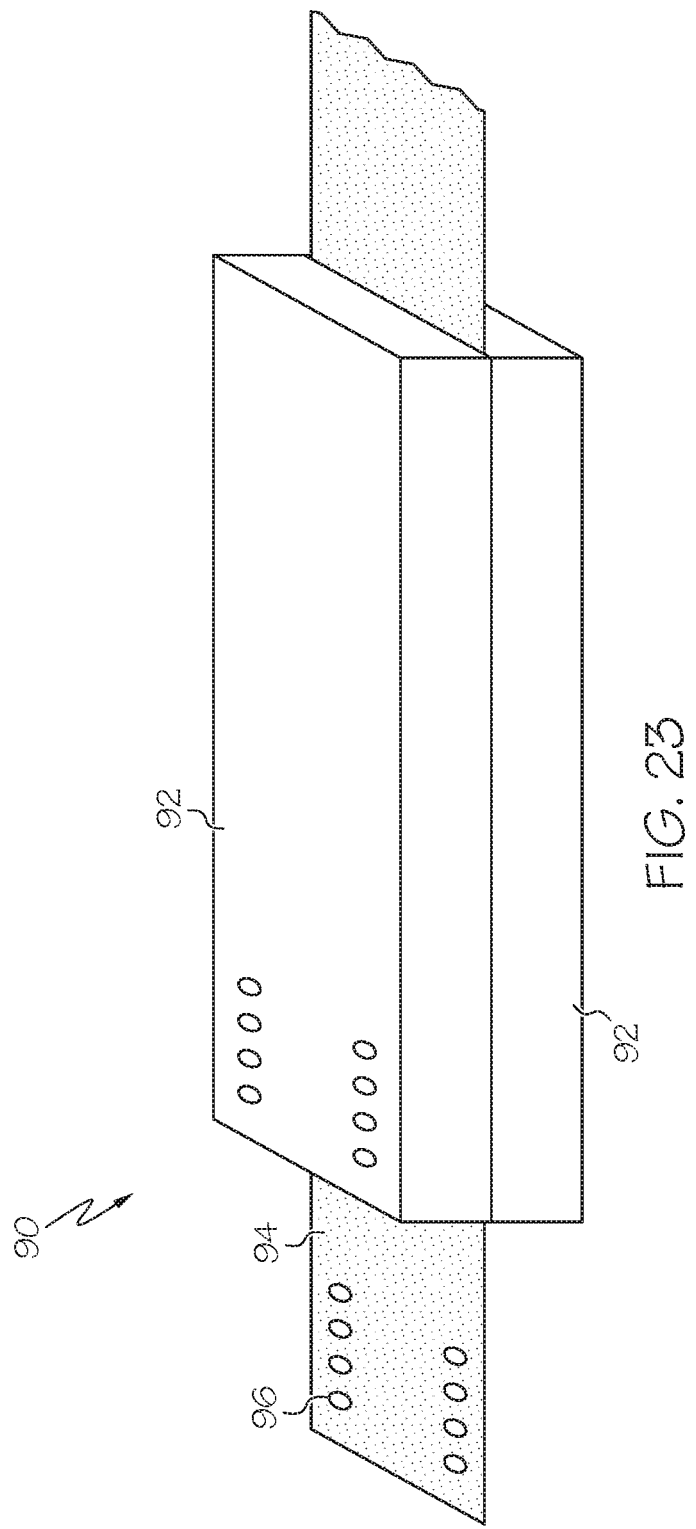
FIG. 23 is view of an exemplary device for forming dimples in a cover.

An exemplary cover template 94 with template dimples 96 is shown in FIG. 23. An exemplary device for forming a cover template 94 is the device 90 shown in FIG. 23. Although the device 90 shown in FIG. 23 has two plates 92, a single plate 92 may be used. One plate 92 has at least one plate dimple or indentation in the surface of the plate.

Method 7

An exemplary method of forming a prosthesis 10 with at least one dimple 40 comprises one or more of the following: mounting the scaffolding 18 on a mandrel 84 with a recess 86; applying coating material to the mounted scaffolding; wherein the scaffolding is positioned a distance above the recess 86; wherein the scaffolding 18 conforms to the recess 86; wherein dip-coating is used for applying the material of the cover 60; wherein spray-coating is used for applying the material of the cover 60; wherein the material of the cover 60 comprises silicone; and combinations thereof.

Figure 22:
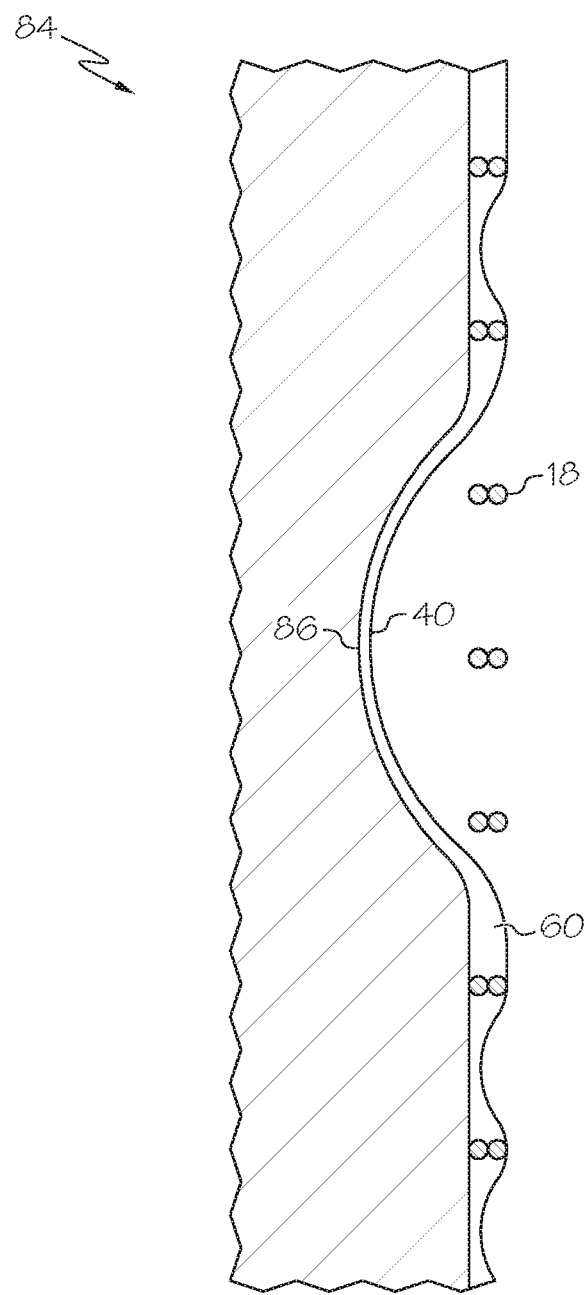
FIG. 22 is a schematic cross-sectional view of an exemplary coating mandrel.

A schematic example of a mandrel 84 with a recess 86 is provided in FIG. 22.

Method 8

An exemplary method of forming a prosthesis 10 with a dimple 40 comprises one or more of the following: securing a cover 60 with a dimple 40 to an expandable prosthesis 10, the expandable prosthesis defining a plurality of scaffolding openings 24; wherein the cover 60 forms a prosthesis outer surface 16; wherein the cover 60 is secured to the prosthesis by an adhesive; wherein the cover 60 is secured to the prosthesis by a suture; wherein the scaffolding 18 has a uniform diameter; and combinations thereof.

Method 9

An exemplary method of forming a prosthesis 10 with a reinforced dimple 40 comprises one or more of the following: forming a scaffolding 18 comprising a first region with a first diameter and a second region with a second diameter greater than the first diameter; applying a cover material to the scaffolding; wherein the coated first region is a reinforced dimple; wherein the first region extends around the circumference of the prosthesis.

Method 10

An exemplary method of forming a prosthesis 10 with a dimple patch 68 comprises one or more of the following: forming an opening in a side wall of an expandable prosthesis 10; and attaching a dimple patch 68 to the expandable prosthesis so that the dimple patch covers the opening formed in the side wall, wherein the dimple patch is sized to extend inward into the opening of the side wall when the prosthesis is implanted; wherein forming the opening in the side wall is part of forming the scaffolding of the expandable prosthesis; wherein forming the opening in the side wall comprises removing a part of a scaffolding of the prosthesis; wherein the expandable prosthesis is selected from the group consisting of stents; covered stents; and stent-grafts; wherein the dimple patch is reinforced with a secondary scaffolding, the secondary scaffolding positioned between an inner surface and an outer surface of the dimple patch; wherein the dimple patch comprises silicone; and combinations thereof.

Materials

Cover/Dimple Patch

Suitable materials for the cover 60 and the dimple patch include any other type of material that prevents tissue ingrowth therethrough. In one aspect, the cover 60 is non-porous. Non-limiting examples include silicone elastomers, polyurethane, polystyrene-polyisobutylene-polystyrene triblock copolymer (SIBS), polytetrafluroethylene (PTFE), expanded polytetrafluroethylene (ePTFE), and combinations thereof.

Scaffolding/Separate Filament/Scaffolding Patch

The scaffolding 18, the separate filament 48, and scaffolding patch may be balloon expandable or self-expandable, and may be made from any suitable biocompatible materials including one or more polymers, one or more metals or combinations of polymer(s) and metal(s). Examples of suitable metals include, but are not limited to, stainless steel, titanium, tantalum, platinum, tungsten, gold and alloys of any of the above-mentioned metals. Examples of suitable alloys include platinum-iridium alloys; cobalt-chromium alloys including Elgiloy and Phynox; nickel-cobalt-chromium-molybdenum alloy such as MP35N; and nickel-titanium alloys, for example, Nitinol; and doped ternary alloys such as NiTiCo and NiTiCr.

The scaffolding 18 may be made of shape memory materials (metallic such as Nitinol; or polymeric, e.g. polyethylene terephthalate (PET)); or may be made of materials which are plastically deformable. Shape memory materials may be processed to have a shape memory effect or super-elasticity. In the case of shape memory materials with a shape memory effect, the prosthesis may be processed to have a memorized shape, and then deformed to a reduced diameter shape for delivery to a body lumen. The prosthesis may restore itself to its memorized shape in a body lumen upon being heated to a transition temperature and having any restraints removed therefrom.

The scaffolding 18 may be made of biodegradable or bioabsorbable materials will undergo breakdown or decomposition into harmless compounds as part of a normal biological process. Suitable biodegradable or bioabsorbable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers.

Therapeutic Agents

Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent is delivered by a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the disclosure such that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the disclosure. Those skilled in the art may recognize other equivalents to the specific embodiment described herein which equivalents are intended to be encompassed by the claims attached hereto.

What is claimed is:

1. A stent comprising:
    a tubular scaffolding formed by at least one interwoven filament, the tubular scaffolding expandable from a compressed delivery state to an expanded implanted state, the scaffolding extending between first and second ends of the stent, the scaffolding having an outer surface and an inner surface, the inner surface defining a lumen of the tubular scaffolding, wherein the at least one interwoven filament of the scaffolding defines a plurality of openings between filament crossings of the at least one interwoven filament, the plurality of openings extending between the inner and outer surfaces; and
    a cover disposed on the scaffolding, the stent including a first portion in which the cover covers and contacts at least one of the inner and outer surfaces of the scaffolding, and a second portion in which a radially outward surface of a section of the cover extends inward of the scaffolding and is spaced radially inward away from the inner surface of the scaffolding to define a void between the radially outward surface of the cover and the inner surface of the scaffolding, thereby creating a controlled tissue ingrowth feature within the openings, wherein the scaffolding has a constant outer diameter throughout the first and second portions.

2. The stent of claim 1, wherein the controlled tissue ingrowth feature is formed only by the cover.

3. The stent of claim 1, wherein in the first portion of the stent, the cover covers only the outer surface of the scaffolding.

4. The stent of claim 3, wherein an outer surface of the stent is defined only by the cover.

5. The stent of claim 1, wherein the first and second portions alternate along a length of the stent.

6. The stent of claim 1, wherein in the first portion of the stent, the cover covers both the inner and outer surfaces of the scaffolding.

7. The stent of claim 1, wherein the section of the cover defining the controlled tissue ingrowth feature spans a single scaffold opening.

8. The stent of claim 7, wherein the single scaffold opening has a size greater than scaffold openings in the first portion of the stent.

9. The stent of claim 1, wherein the section of the cover defining the controlled tissue ingrowth feature spans a plurality of scaffold openings.

10. The stent of claim 1, wherein the cover occludes the scaffolding openings and prevents tissue ingrowth into a lumen of the stent.

11. The stent of claim 1, wherein the scaffolding comprises a braided mesh of filaments.

12. The stent of claim 11, wherein at least one of the filaments extending through the second portion is exposed from the cover.

13. The stent of claim 1, wherein the second portion includes a plurality of controlled tissue ingrowth features, wherein in each controlled tissue ingrowth feature, the outer surface of the cover extends inward and is spaced radially inward away from the inner surface of the scaffolding.

14. The stent of claim 1, wherein an entirety of the cover has a uniform thickness.

\* \* \* \* \*